United States Patent
Koskimäki et al.

(10) Patent No.: US 12,216,829 B2
(45) Date of Patent: Feb. 4, 2025

(54) RING-INPUTTED COMMANDS

(71) Applicant: Oura Health Oy, Oulu (FI)

(72) Inventors: Heli Koskimäki, Oulu (FI); Johanna Still, Oulu (FI); Mari Karsikas, Oulu (FI); Alec Singleton, Toronto (CA); Petteri Lajunen, Oulu (FI); Henri Huttunen, Haukipudas (FI); Veli-Pekka Halme, Oulu (FI); Marcus Ziade, Helsinki (FI); Janne Kukka, Santa Barbara, CA (US)

(73) Assignee: Oura Health Oy, Oulu (FI)

( * ) Notice: Subject to any disclaimer, the term of this patent is extended or adjusted under 35 U.S.C. 154(b) by 29 days.

(21) Appl. No.: 17/729,291

(22) Filed: Apr. 26, 2022

(65) Prior Publication Data
US 2023/0341944 A1    Oct. 26, 2023

(51) Int. Cl.
*G06F 3/01*     (2006.01)
*A61B 5/00*    (2006.01)
*G06F 1/16*     (2006.01)
*G06F 3/048*   (2013.01)

(52) U.S. Cl.
CPC ............ *G06F 3/017* (2013.01); *A61B 5/6826* (2013.01); *A61B 5/7275* (2013.01); *A61B 5/7435* (2013.01); *G06F 1/163* (2013.01); *G06F 3/014* (2013.01); *G06F 3/048* (2013.01)

(58) Field of Classification Search
CPC .......... G06F 3/017; G06F 1/163; G06F 3/014; G06F 3/048; G06F 1/1694; A61B 5/6826; A61B 5/7275; A61B 5/7435
See application file for complete search history.

(56) References Cited

U.S. PATENT DOCUMENTS

| | | | |
|---|---|---|---|
| 8,010,911 B2* | 8/2011 | Sohn | G06F 3/0346 715/863 |
| 9,141,194 B1* | 9/2015 | Keyes | G06F 3/014 |
| 9,595,171 B2* | 3/2017 | Hurtig | G06F 3/0487 |
| 10,139,906 B1* | 11/2018 | Bai | G06F 3/014 |
| 11,093,043 B1* | 8/2021 | Graber | G06F 1/163 |
| 11,366,529 B1* | 6/2022 | Reynolds | G06F 3/014 |
| 11,462,107 B1* | 10/2022 | Sanchez | G06F 3/014 |
| 2011/0210931 A1* | 9/2011 | Shai | G06F 3/03547 345/173 |
| 2014/0296935 A1* | 10/2014 | Ferree | A61N 1/3603 607/46 |
| 2015/0116079 A1* | 4/2015 | Mishra | G07C 9/257 340/5.52 |

(Continued)

*Primary Examiner* — Patrick F Riegler
(74) *Attorney, Agent, or Firm* — Holland & Hart LLP

(57) ABSTRACT

Methods, systems, and devices for device-inputted commands are described. A system may receive physiological data, including motion data, associated with a user from a wearable device worn by the user and may detect multiple motion pulses based on the motion data, where each motion pulse includes motion data that exceeds a motion threshold. The system may additionally identify an input command pattern comprising at least one motion pulse preceded and followed by a static period in a time domain. Additionally, the system may identify one or more user inputs based on the input command pattern matching a reference command pattern and generate one or more instructions based on identifying the one or more user inputs.

20 Claims, 9 Drawing Sheets

(56) References Cited

U.S. PATENT DOCUMENTS

| | | | | |
|---|---|---|---|---|
| 2015/0149956 A1* | 5/2015 | Kempinski | ............ | G06F 3/0485 |
| | | | | 715/784 |
| 2015/0277559 A1* | 10/2015 | Vescovi | ................. | G06F 3/017 |
| | | | | 345/173 |
| 2016/0202759 A1* | 7/2016 | Choi | ...................... | G06F 3/038 |
| | | | | 345/156 |
| 2016/0313798 A1* | 10/2016 | Connor | ................ | A61B 5/1125 |
| 2017/0090590 A1* | 3/2017 | Shimotono | ............ | G04G 21/00 |
| 2017/0228025 A1* | 8/2017 | Hall | ........................ | G06F 3/017 |
| 2017/0249009 A1* | 8/2017 | Parshionikar | ........... | G06F 3/017 |
| 2017/0364156 A1* | 12/2017 | Kim | ........................ | G06F 1/163 |
| 2018/0120892 A1* | 5/2018 | von Badinski | ......... | G06F 3/014 |
| 2019/0022386 A1* | 1/2019 | Gozani | .................. | G06F 1/163 |
| 2020/0004415 A1* | 1/2020 | Warren | ................... | G06F 3/162 |
| 2020/0249752 A1* | 8/2020 | Parshionikar | ........... | G06F 3/016 |
| 2021/0026333 A1* | 1/2021 | Kim | .................. | G05B 19/4155 |
| 2021/0085245 A1* | 3/2021 | Cihan | .................. | A61B 5/6844 |
| 2022/0101613 A1* | 3/2022 | Rockel | ................... | G06F 3/013 |
| 2022/0211284 A1* | 7/2022 | Kim | ...................... | A61B 5/0205 |
| 2022/0233142 A1* | 7/2022 | Hasan | ................... | A61B 5/681 |
| 2023/0043018 A1* | 2/2023 | Wai | ...................... | A61B 5/1113 |

\* cited by examiner

RING-INPUTTED COMMANDS

FIELD OF TECHNOLOGY

The following relates to wearable devices and data processing, including ring-inputted commands.

BACKGROUND

Some wearable devices may be configured to collect data from users. For example, a wearable device may include one or more sensors that collect physiological data from a user. Some systems associated with the wearable devices may also be able to perform various actions, such as providing certain health insights to users.

DETAILED DESCRIPTION

Figure 1:
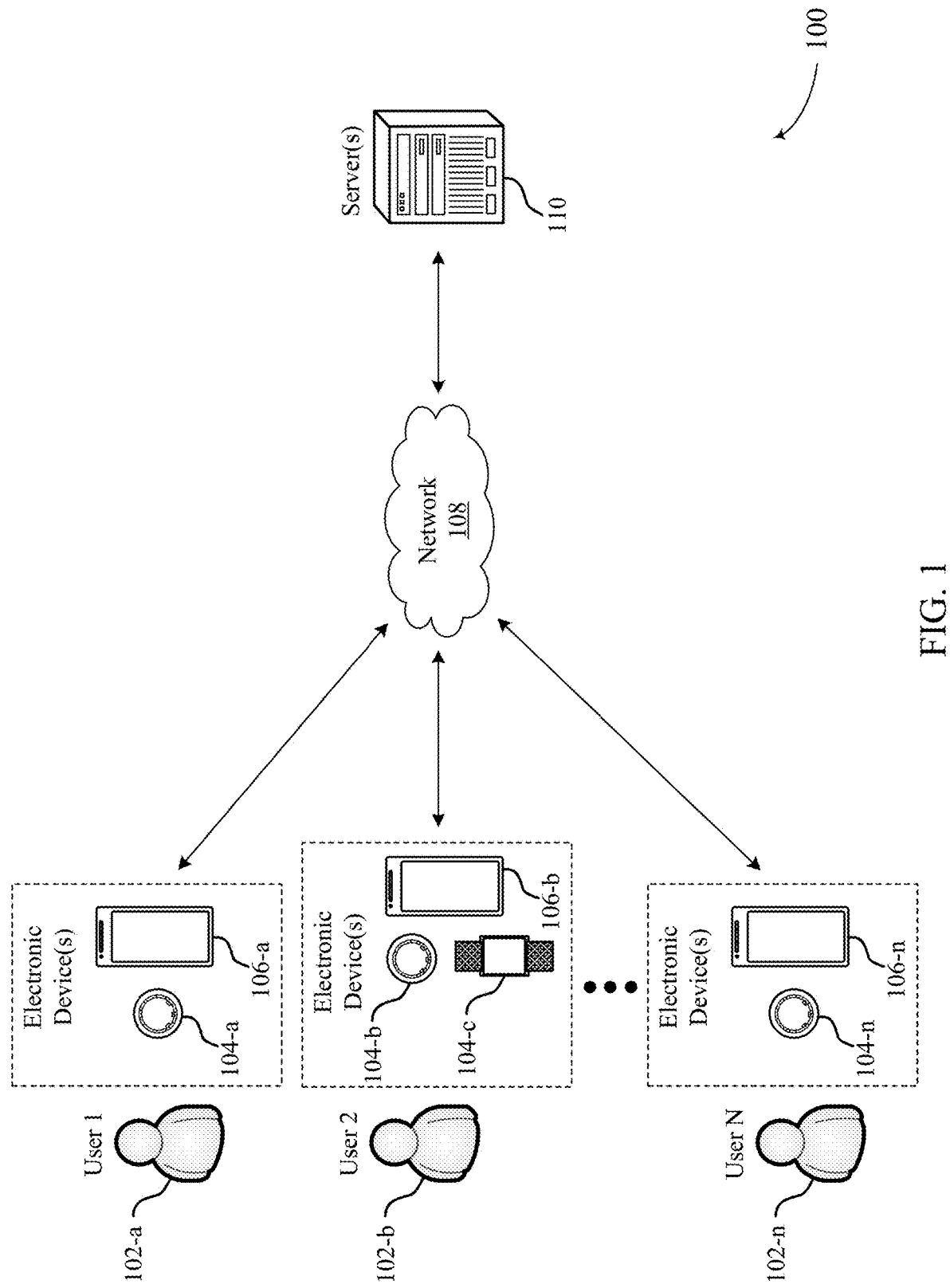
FIG. 1 illustrates an example of a system that supports ring-inputted commands in accordance with aspects of the present disclosure.

A user may use a device, for example, a wearable ring device to collect, monitor, and track physiological data of the user based on sensor measurements of the wearable ring device. Examples of physiological data may include temperature data, heart rate data, photoplethysmography (PPG) data, and the like. The physiological data collected, monitored, and tracked via the wearable ring device may be used to gain health insights about the user, such as the user's sleeping patterns, activity patterns, and the like. However, a user may want to control the wearable device, or input commands associated with the wearable device.

For example, a user may wear a wearable device associated with a mobile device, where the mobile device may be used to view and input information or commands associated with the wearable device. However, in some circumstances, it may be inconvenient or impossible for the user to access the mobile device, such as in cases where the mobile device is located some distance from the user. The inability to access the mobile device (e.g., an application executable on the mobile device) may prevent the user from being able to control the wearable device. Moreover, even in cases where users are able to easily access a mobile device, requiring users to open up a wearable application to manually input information associated with a wearable device may significantly reduce a frequency that users input information and interact with the application, as users may simply forget to access the mobile device or be unwilling to take time away from their daily routine to manually open up an application and input information.

Some wearable devices include buttons or screens to enable users to input commands directly via the wearable devices. However, other wearable devices, such as wearable ring devices, do not include buttons, screens, or other traditional means for inputting commands. Moreover, buttons, screens, and other traditional means for inputting commands may detract from the aesthetic appeal of a wearable device, and may therefore be undesirable in some circumstances. In the context of wearable devices that do not include buttons or screens to enable users to input commands directly via the wearable devices themselves, users may resort to inputting commands via mobile devices which may result in less frequent interaction with the wearable device, as described herein. As such, conventional techniques for inputting commands and other information via wearable devices and associated mobile devices are deficient.

Accordingly, aspects of the present disclosure support techniques that enable users to easily and efficiently input commands directly via a wearable device, such as a wearable ring device, by performing some action or movement, such as by tapping or rotating the wearable device, performing some hand gesture, and the like. In other words, aspects of the present disclosure support a method of identifying a device inputted (e.g., ring-inputted) command pattern and selectively generating instructions based on the inputted command pattern.

Instructions generated in response to an identified command pattern may be used to perform a wide variety of actions, including starting/stopping workouts, authorizing a transaction, authenticating a user, tagging events (e.g., tagging alcohol consumption, tagging a meditation), controlling external devices (e.g., turning a speaker on/off, adjusting a smart thermostat), and the like. In other words, techniques described herein may be used to identify device-inputted commands (e.g., ring-inputted commands) that are configured to control or modify the wearable device itself, a wearable application associated with the wearable device, an external device, or any combination thereof.

In particular, aspects of the present disclosure are directed to techniques that enable wearable devices to differentiate normal user movement and activity throughout the day from movement (e.g., taps, rotations, gestures) that is intended as user inputted commands. For example, a system may collect physiological data associated with a user, including motion data collected via an accelerometer sensor of a wearable ring device. In some cases, a user may input a command pattern by interacting with the wearable ring device (e.g., performing an action associated with the wearable ring device) to generate one or more motion pulses (e.g., motion data that exceeds a motion threshold). A user interaction with the wearable ring device may include, but is not limited to, tapping on the ring wearable device, rotating the ring wearable device, performing a hand gesture, or any combination thereof. The wearable ring device may identify the one or more motion pulses and further identify the input command pattern based on the one or more motion pulses. An input command pattern may include motion data collected throughout some time interval that includes at least one motion pulse.

Continuing with the same example, the system may compare the input command pattern to reference command patterns (e.g., stored in a command library), where each reference command pattern corresponds to a user input (e.g., command). That is, the system may match the input command pattern to a reference command pattern to identify one or more user inputs. By matching the input command pattern to a reference command pattern in order to identify a valid user input, techniques described herein may be able to differentiate "normal" user movement throughout the day from user movement that is intended as a user input.

If the input command pattern matches a reference command pattern, the wearable ring device may identify that the user inputted a user input, and may generate one or more instructions based on the user input. For example, upon identifying a user input, the system may tag an event or cause a device associated with the wearable ring device to perform an action based on the one or more instructions. For instance, the three taps on the wearable ring device may correspond to a first reference command pattern that is associated with a first user input (e.g., user input to tag caffeine consumption), while four taps on the wearable ring device may correspond to a second reference command pattern that is associated with a second user input (e.g., adjust a smart thermostat).

Upon identifying a user input (e.g., based on determining an input command pattern matches a pre-defined reference command pattern), a system described herein may generate instructions (e.g., signals) to perform any number of actions. Actions that may be performed upon identifying a user input may include, but are not limited to, tagging information or events (e.g., tagging alcohol/caffeine consumption), starting/ ending a workout, causing a user device to take a picture, adjusting or activating/deactivating external devices (e.g., speakers, smart lights, smart appliances, thermostats, other household electronics), performing an authentication procedure (e.g., verifying a primary identification number (PIN) to identify/authenticate the user or perform a transaction, authenticating user to unlock or open doors), activating sensors of a wearable device (e.g., performing an electrocardiogram (ECG) measurement) and the like. Moreover, in some implementations, users may be able to manually input reference command patterns and associated instructions/ actions. In other words, aspects of the present disclosure may enable users to customize user inputs (e.g., tapping patterns) and actions that are performed upon detection of the customized user inputs.

While much of the present disclosure is described in the context of tapping the wearable ring device, this is not to be regarded as a limitation of the present disclosure. Indeed, it is contemplated herein that any interaction with the wearable ring device, including tapping, may be associated with an input command pattern. In this regard, other interactions with the wearable ring device may be used for receiving user inputs via a wearable device, including rotating the wearable device, performing a gesture (e.g., hand movement) with the wearable device, and the like.

Aspects of the disclosure are initially described in the context of systems supporting physiological data collection from users via wearable devices. Aspects of the disclosure are then described in the context of an example command pattern and an example graphical user interface (GUI). Aspects of the disclosure are further illustrated by and described with reference to apparatus diagrams, system diagrams, and flowcharts that relate to ring-inputted commands.

FIG. 1 illustrates an example of a system 100 that supports ring-inputted commands in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/ goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-*a* (User 1) may operate, or may be associated with, a wearable device 104-*a* (e.g., ring 104-*a*) and a user device 106-*a* that may operate as described herein. In this example, the user device 106-*a* associated with user 102-*a* may process/store physiological parameters measured by the ring 104-*a*. Comparatively, a second user 102-*b* (User 2) may be associated with a ring 104-*b*, a watch wearable device 104-*c* (e.g., watch 104-*c*), and a user device 106-*b*, where the user device 106-*b* associated with user 102-*b* may process/store physiological parameters measured by the ring 104-*b* and/or the watch 104-*c*. Moreover, an nth user 102-*n* (User N) may be associated with an arrangement of electronic devices described herein (e.g., ring 104-*n*, user device 106-*n*). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more LEDs (e.g., red LEDs, green LEDs) that emit light on the palm-side of a user's finger to collect physiological data based on arterial blood flow within the user's finger. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-*a* associated with the first user 102-*a* may be communicatively coupled to the user device 106-*a*, where the user device 106-*a* is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time during which a user 102 is asleep, and classify periods of time during which the user 102 is asleep into one or more sleep stages (e.g., sleep stage classification). For example, as shown in FIG. 1, User 102-*a* may be associated with a wearable device 104-*a* (e.g., ring 104-*a*) and a user device 106-*a*. In this example, the ring 104-*a* may collect physiological data associated with the user 102-*a*, including temperature, heart rate, HRV, respiratory rate, and the like. In some aspects, data collected by the ring 104-*a* may be input to a machine learning classifier, where the machine learning classifier is configured to determine periods of time during which the user 102-a is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-a via a GUI of the user device 106-a. Sleep stage classification may be used to provide feedback to a user 102-a regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-a via the wearable device 104-a. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g. in a hypothetical culture with 12 day "weeks", 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques for ring-inputted commands. In particular, the system 100 illustrated in FIG. 1 may support techniques for identifying an input command pattern based on motion data associated with a user 102. For example, as shown in FIG. 1, a user 102-a may be associated with a ring 104-a and a user device 106-a. In this example, the ring 104-a may collect physiological data associated with the user 102-a, including motion data collected via one or more acceleration sensors (e.g., motion sensors) on the ring 104-a. The system 100 may identify one or more motion pulses based on the motion data, where each motion pulse includes motion data that exceeds a motion threshold (e.g., tap threshold described with reference to FIG. 3). For example, the user 102-a may tap the ring 104-a multiple times generating multiple motion pulses, where each motion pulse corresponds to a tap on the ring 104-a. Detection of the motion pulses may be performed by any of the components of the system 100, including the ring 104-a, the user device 106-a, one or more servers 110, or any combination thereof.

Continuing with the same example, the system 100 may identify an input command pattern based on the motion pulses and identify a user input based on the input command pattern matching a reference command pattern. For example, the user 102-a may tap the ring 104-a three times and the system 100 may identify the three taps as an input command pattern. Additionally, the system 100 may identify that the input command pattern of three taps matches a reference command pattern of three taps, where the reference command pattern is associated with a user input. As such, the system 100 may identify the associated user input based on the input command pattern matching the reference command pattern (e.g., identify a valid user input), and generate instructions based on the user input. In some cases, the instructions may cause the system 100 to display a confirmation of the user input via a GUI of the user device 106-a.

In some implementations, the instructions may cause the system 100 to prompt the user 102-a (e.g., via a GUI of the user device 106-a) to confirm the user input. For example, the user 102-a may tap the ring 104-a three times to tag that the user 102-a has consumed alcohol and the system 100 may prompt the user 102-a to confirm the alcohol consumption. Additionally, the system 100 may prompt the user 102-a to provide additional data associated with the user input. For example, the system 100 may prompt the user to provide additional data associated with the type of alcohol consumed (e.g., beer, wine, etc.). In other cases, the system 100 may automatically confirm the user input without additional prompting or confirmation from the user.

In some implementations, upon identifying a valid user input, the system 100 may cause the ring 104-a, the user device 106-a, an external device, or any combination thereof to perform an action based on the user input (e.g., based on the instructions corresponding to the identified user input). For example, after swiping a credit card to perform a payment or transaction, the user 102-a may perform an input command pattern via the ring 104-a associated with an authentication procedure (e.g., a primary identification number (PIN) input command pattern). For instance, the user may tap the ring 104-a using the PIN input command pattern. Thus, the system 100 may identify the PIN input command pattern matches a reference command pattern associated with authenticating the user 102-a and may generate one or more instructions to authorize the user device 106-a to complete the payment based on the authentication.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
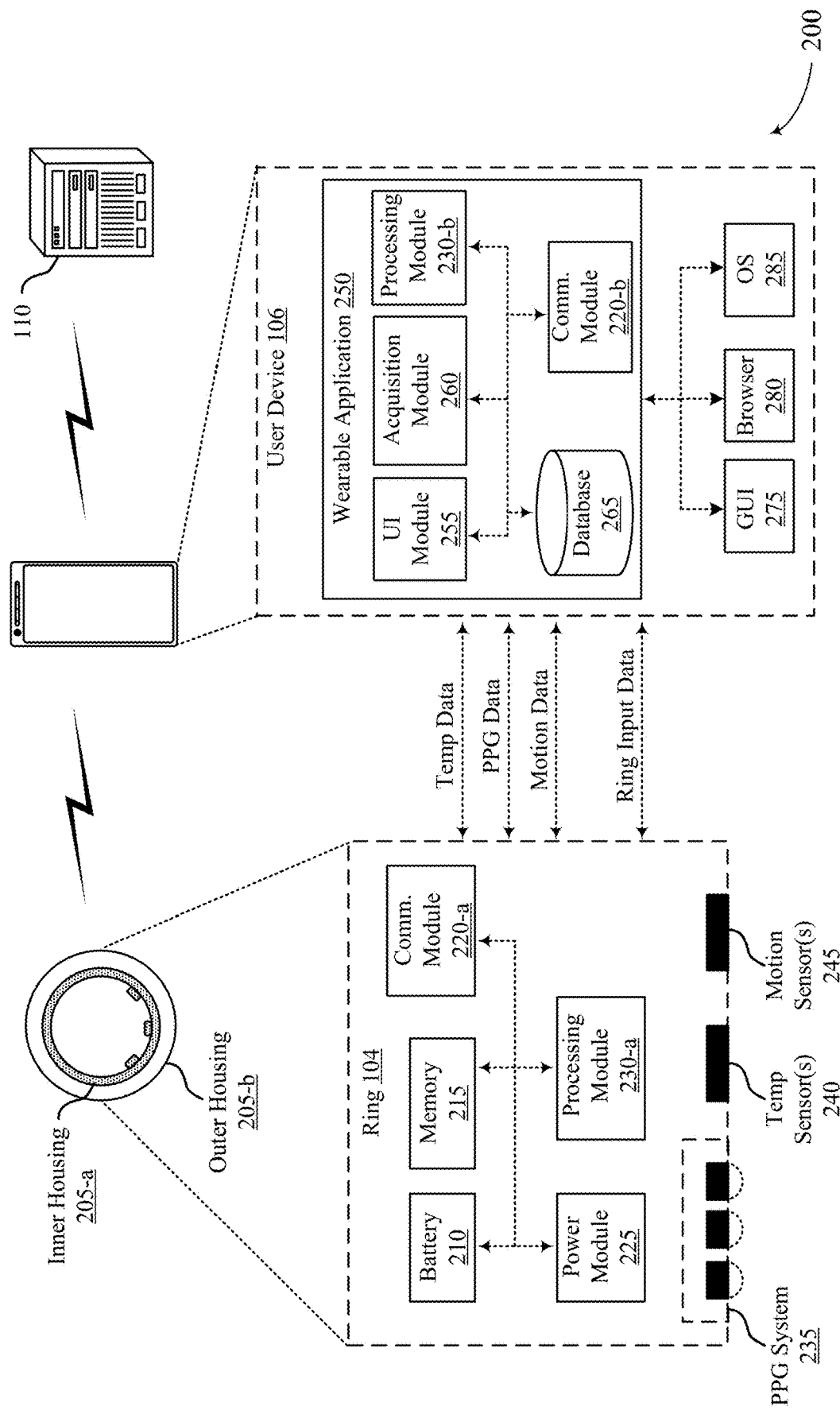
FIG. 2 illustrates an example of a system that supports ring-inputted commands in accordance with aspects of the present disclosure.

FIG. 2 illustrates an example of a system 200 that supports ring-inputted commands in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels, and the like.

The system 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, PPG data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-a and an outer housing 205-b. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-a, a memory 215, a communication module 220-a, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using a clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-b component (e.g., a shell) and an inner housing 205-a component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-b (e.g., a metal outer housing 205-b). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-b may be fabricated from one or more materials. In some implementations, the outer housing 205-b may include a metal, such as titanium, that may provide strength and abrasion resistance at a relatively light weight. The outer housing 205-b may also be fabricated from other materials, such polymers. In some implementations, the outer housing 205-b may be protective as well as decorative.

The inner housing 205-a may be configured to interface with the user's finger. The inner housing 205-a may be formed from a polymer (e.g., a medical grade polymer) or other material. In some implementations, the inner housing 205-a may be transparent. For example, the inner housing 205-a may be transparent to light emitted by the PPG light emitting diodes (LEDs). In some implementations, the inner housing 205-a component may be molded onto the outer housing 205-a. For example, the inner housing 205-a may include a polymer that is molded (e.g., injection molded) to fit into an outer housing 205-b metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-a of the ring 104 may include one or more processors (e.g., processing units), microcontrollers, digital signal processors, systems on a chip (SOCs), and/or other processing devices. The processing module 230-a communicates with the modules included in the ring 104. For example, the processing module 230-a may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-a may communicate with the memory 215. The memory 215 may include computer-readable instructions that, when executed by the processing module 230-a, cause the processing module 230-a to perform the various functions attributed to the processing module 230-a herein. In some implementations, the processing module 230-a (e.g., a microcontroller) may include additional features associated with other modules, such as communication functionality provided by the communication module 220-a (e.g., an integrated Bluetooth Low Energy transceiver) and/or additional onboard memory 215.

The communication module 220-a may include circuits that provide wireless and/or wired communication with the user device 106 (e.g., communication module 220-b of the user device 106). In some implementations, the communication modules 220-a, 220-b may include wireless communication circuits, such as Bluetooth circuits and/or Wi-Fi circuits. In some implementations, the communication modules 220-a, 220-b can include wired communication circuits, such as Universal Serial Bus (USB) communication circuits. Using the communication module 220-a, the ring 104 and the user device 106 may be configured to communicate with each other. The processing module 230-a of the ring may be configured to transmit/receive data to/from the user device 106 via the communication module 220-a. Example data may include, but is not limited to, motion data, temperature data, pulse waveforms, heart rate data, HRV data, PPG data, and status updates (e.g., charging status, battery charge level, and/or ring 104 configuration settings). The processing module 230-a of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or which supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during 104 charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during 104 charging, and under voltage during 104 discharge. The power module 225 may also include electro-static discharge (ESD) protection.

The one or more temperature sensors 240 may be electrically coupled to the processing module 230-a. The temperature sensor 240 may be configured to generate a temperature signal (e.g., temperature data) that indicates a temperature read or sensed by the temperature sensor 240. The processing module 230-a may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-a) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-a may use to determine the temperature. As another example, in cases where the temperature sensor 240 includes a passive sensor, the processing module 230-a (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-a may sample the user's temperature over time. For example, the processing module 230-a may sample the user's temperature according to a sampling rate. An example sampling rate may include one sample per second, although the processing module 230-a may be configured to sample the temperature signal at other sampling rates that are higher or lower than one sample per second. In some implementations, the processing module 230-a may sample the user's temperature continuously throughout the day and night. Sampling at a sufficient rate (e.g., one sample per second) throughout the day may provide sufficient temperature data for analysis described herein.

The processing module 230-a may store the sampled temperature data in memory 215. In some implementations, the processing module 230-a may process the sampled temperature data. For example, the processing module 230-a may determine average temperature values over a period of time. In one example, the processing module 230-a may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during 104 exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-a near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-a may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-a may sample the sensors at different rates and average/store different values for the different sensors. In some implementations, the processing module 230-a may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-a may sample the PPG signal and determine a user's pulse waveform based on the PPG signal. The processing module 230-a may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 in which the optical receiver(s) receive transmitted light that is reflected through the region of the user's finger. In some implementations, the PPG system 235 may be configured as a transmissive PPG system 235 in which the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-a may control one or both of the optical transmitters to transmit light while sampling the PPG signal generated by the optical receiver. In some implementations, the processing module 230-a may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-a may store the pulse waveform in memory 215 in some implementations. The processing module 230-a may process the pulse waveform as it is generated and/or from memory 215 to determine user physiological parameters described herein.

The processing module 230-a may determine the user's heart rate based on the pulse waveform. For example, the processing module 230-a may determine heart rate (e.g., in beats per minute) based on the time between peaks in the pulse waveform. The time between peaks may be referred to as an interbeat interval (IBI). The processing module 230-a may store the determined heart rate values and IBI values in memory 215.

The processing module 230-a may determine HRV over time. For example, the processing module 230-a may determine HRV based on the variation in the IBIs. The processing module 230-a may store the HRV values over time in the memory 215. Moreover, the processing module 230-a may determine the user's respiratory rate over time. For example, the processing module 230-a may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-a may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BM1160 inertial micro electro-mechanical system (MEMS) sensor that may measure angular rates and accelerations in three perpendicular axes.

The processing module 230-a may sample the motion signals at a sampling rate (e.g., 50 Hz) and determine the motion of the ring 104 based on the sampled motion signals. For example, the processing module 230-a may sample acceleration signals to determine acceleration of the ring 104. As another example, the processing module 230-a may sample a gyro signal to determine angular motion. In some implementations, the processing module 230-a may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-a may compress the data stored in memory 215. For example, the processing module 230-a may delete sampled data after making calculations based on the sampled data. As another example, the processing module 230-a may average data over longer periods of time in order to reduce the number of stored values. In a specific example, if average temperatures for a user over one minute are stored in memory 215, the processing module 230-a may calculate average temperatures over a five minute time period for storage, and then subsequently erase the one minute average temperature data. The processing module 230-a may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during 104 portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-b, a communication module 220-b, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time in which the respective users typically sleep.

In some implementations, each overall score for a user for each respective day (e.g., Sleep Score, Readiness Score)

may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the respective devices of the system 200 may support techniques for ring-inputted commands. In particular, the system 200 illustrated in FIG. 2 may support techniques for identifying an input command pattern based on motion data associated with a user. For example, a user may be associated with a ring 104 and a user device 106. In this example, the ring 104 may collect physiological data associated with the user 102, including motion data collected via one or more motion sensors 245 on the ring 104. The system 200 may detect (e.g., identify) multiple motion pulses based on the motion data collected by the one or more sensors 245, where each motion pulse includes motion data that exceeds a motion threshold, as described with reference to FIG. 3. For example, the user may tap the outer housing 205-b of the ring 104 generating motion pulses, each motion pulse corresponding to a tap on the outer housing 205-b of the ring 104. Detection of the motion pulses may be performed by any of the components of the system 100, including the ring 104, the user device 106, one or more servers 110, or any combination thereof.

Continuing with the example above, the system 200 may detect (e.g., identify) an input command pattern based on the identified motion pulses. For the purposes of the present disclosure, the term "input command pattern" may be used to refer to physiological data (e.g., motion data) collected throughout some time period that includes at least one motion pulse. Upon identifying an input command pattern, the system 200 may compare the identified input command pattern with one or more reference command patterns to determine whether the input command pattern matches a reference command pattern. If the system 200 determines that the input command pattern matches a reference command pattern, the system 200 may identify a valid user input, and may generate instructions and/or perform some action associated with the identified user input.

For example, the user may tap the outer housing 205-b three times, and the system 200 may identify the three taps as an input command pattern. Additionally, the system 200 may identify that the input command pattern including three taps matches a reference command pattern from a library of reference command patterns (e.g., command library) stored in a database 265, where the reference command pattern is associated with a user input. The system 200 may identify the associated user input and generate instructions based on the user input. In some cases, the instructions may cause the system 200 to display a confirmation of the user input via a GUI 275 of the user device 106. For instance, the user input may cause the user device 106 to take a picture (e.g., generate instructions that cause a camera of the user device 106 to take a picture). By way of another example, the user input may cause the ring 104, user device 106, and/or servers 110 to tag an event or information (e.g., tag or start/stop a workout, tag stress, tag food consumption).

Figure 3:
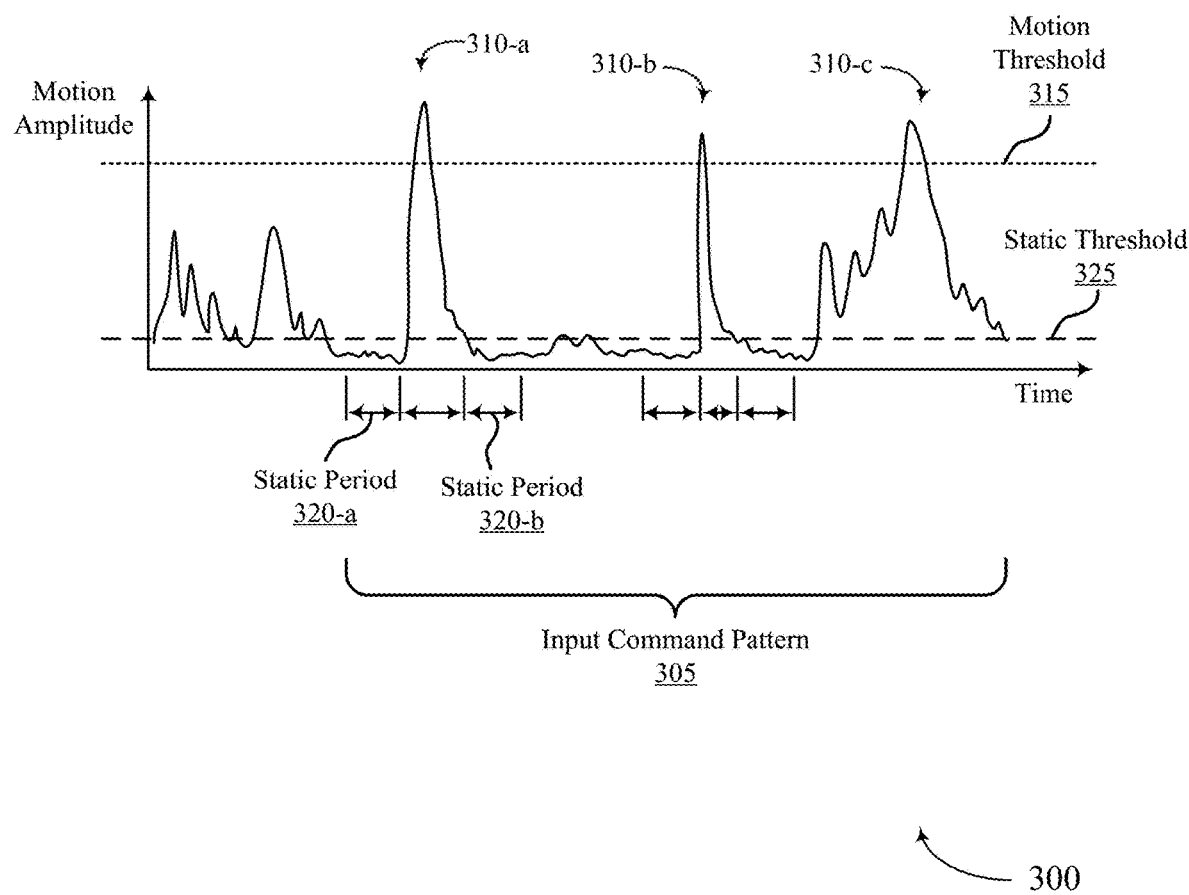
FIG. 3 illustrates an example of a command pattern that supports ring-inputted commands in accordance with aspects of the present disclosure.

FIG. 3 illustrates an example of a command pattern 300 that supports ring-inputted commands in accordance with aspects of the present disclosure. The command pattern 300 may implement, or be implemented by, aspects of the system 100, the system 200, or both.

The command pattern 300 shown in FIG. 3 illustrates an example of an input command pattern 305. The input command pattern 305 may include one or more motion pulses 310 that include motion data (e.g., collected by an motion sensor at a wearable ring device, such as a ring 104, described with reference to FIG. 2) exceeding a motion threshold, such as a motion threshold 315. In other words, each "motion pulse 310" may include motion data that exceeds the motion threshold 315. The motion data resulting in the motion pulses 310 may be based on one or more user interactions with the ring that may include, but are not limited to, tapping the ring 104 (e.g., tapping the ring with the user's finger, tapping the ring 104 on a table or other surface), rotating the ring 104, performing a hand gesture using a hand wearing the ring 104, or any combination thereof. For example, a motion pulse 310-*a* may be detected based on a user tapping the ring 104, producing motion data exceeding the motion threshold 315.

Additionally, a system associated with the ring 104, such as a system 200, may detect a motion pulse 310 based on static periods 320 preceding and following the motion pulse 310 (e.g., to determine a motion pulse 310 is associated with an input command pattern 305 and not accidental motion of the ring 104). In other words, a motion pulse 310 (e.g., motion pulse 310-*a*) that is preceded and followed by static periods 320 may be more likely to be intended as part of an input command pattern 305 (as compared to motion pulses 310 that are not preceded, followed, or both, by static periods 320). The system may detect a static period 320 based on motion data failing to exceed a static threshold 325 (e.g., less than or equal to the static threshold 325). That is, a user may keep the ring 104 still (e.g., motionless) for a period of time before and a period of time after interacting with the ring 104 such that the system 200 may detect the motion pulse 310 generated via the interaction.

For example, the system 200 may detect a static period 320-*a*, followed by the motion pulse 310-*a*, followed by a static period 320-*b*. Thus, the system 200 may determine that the motion pulse 310-*a* is a valid (e.g., intentional) motion pulse 310 and may be associated with the input command pattern 305. In another example, the system 200 may detect a motion pulse 310-*c* based on motion data associated with the motion pulse 310-*c* exceeding the motion threshold 315. However, the system 200 may not detect a static period 320 preceding and/or following the motion pulse 310-*c*. As such, the system 200 may determine that the motion pulse 310-*c* is not a valid motion pulse 310 (e.g., is unintentional, not associated with the input command pattern 305).

In additional or alternative implementations, the system 200 may identify that the motion pulse 310-*c* is part of the input command pattern 305 (despite the motion pulse 310-*c* not being preceded/followed by static periods 320) based on identifying the first motion pulse 310-*a* that is preceded and followed by the static periods 320-*a*, 320-*b*. For instance, in some cases, a user may generate the input command pattern 305 by keeping a ring 104 still (e.g., first static period 320-*a*), tapping the ring 104 (e.g., motion pulse 310-*a*), and keeping the ring 104 still again (e.g., second static period 320-*b*), then tapping the ring 104 twice in rapid succession (e.g., motion pulses 310-*b*, 310-*c*). In this example, the input command pattern 305 may be identified based on the three motion pulses 310-*a*, 310-*b*, and 310-*c*, even though the third motion pulse 310-*c* may not be preceded and/or followed by static periods 320. In other words, the user may initiate the input command pattern 305 by generating the first motion pulse 310-*a* that is preceded and followed by the static periods 320-*a*, 320-*b*, and may perform the rest of the input command pattern 305 by generating motion pulses 310 that may or may not be preceded/followed by static periods 320.

Upon identifying an input command pattern 305, the system 200 may compare the input command pattern 305 to one or more reference command patterns, where each reference command pattern is associated with a user input. If the input command pattern 305 matches a reference command pattern, the system 200 (e.g., ring 104, user device 106, servers 110) may generate instructions (e.g., perform one or more actions) associated with the user input corresponding to the matching reference command pattern. By matching the input command pattern 305 to a reference command pattern in order to identify a valid user input, techniques described herein may be able to differentiate from "normal" user movement throughout the day from user movement that is intended as a user input.

In some cases, the system 200 may match an input command pattern 305 to a reference command pattern based on a duration of the static periods 320 in the input command pattern 305 matching a duration of the static periods 320 in the reference command pattern (e.g., a duration of the input command pattern 305 matches a duration of the reference command pattern). In other words, the system 200 may determine that the input command pattern 305 matches a reference command pattern based on time offsets between the first motion pulse 310-*a* and additional motion pulses 310-*b*, 310-*c* in the input command pattern 305 being within a variation threshold (e.g., within a range) of the time offset between a first motion pulse 310 and additional motion pulses 310 in the reference command pattern. In other words, the system 200 may compare a relative timing of motion pulses 310 within an input command pattern 305 to a relative timing of motion pulses 310 within a reference command pattern to determine whether or not the input command pattern 305 matches the reference command pattern.

In some embodiments, the system 200 may detect a motion pulse 310 based on a static period 320 beginning within a time threshold (e.g., default time threshold) following the peak of an associated motion pulse 310. For example, if the system 200 detects a motion pulse 310 and fails to detect a static period 320 within one second of detecting a peak of the motion pulse 310, the system 200 may determine that the static period 320 is not associated with the motion pulse 310 (e.g., the motion pulse 310 may be invalid). Additionally or alternatively, the system 200 may detect an input command pattern 305 based on a static period 320 satisfying an initial time threshold prior to a first motion pulse 310 (e.g., a user may keep the ring 104 motionless prior to performing an input command pattern 305). That is, an input command pattern 305 may begin with a static period 320 satisfying a default or user defined time threshold. For example, the system 200 may detect the input command pattern 305 based on the static period 320-*a* being at least one second in duration (e.g., where the one second time threshold is based on a default or user-inputted setting).

In some cases, the duration of the static periods 320 of the reference command pattern may be based on one or more default durations (e.g., default system 200 parameters). For example, the system 200 may define a default duration between taps of one second with a variation threshold of half a second. Additionally, a reference command pattern may include two taps on the ring 104. As such, the system 200 may determine the input command pattern 305 matches the reference command pattern based on the duration of the static period 320-*b* between the first motion pulse 310-*a* and the second motion pulse 310-*b* being between half a second and one and a half seconds in length (e.g., duration). Additionally or alternatively, the duration of the static periods 320 in a reference command pattern may be based on user defined durations. That is, the system 200 may allow the user to extend or shorten the default durations. For example, a user may define a reference command pattern including two taps followed by a pause of 2 seconds before a third tap. As such, the reference command pattern may be defined as a first motion pulse 310, followed by a first static period 320 of default duration, followed by a second motion pulse 310, followed by a second static period 320 of two second duration, followed by a third motion pulse 310.

Additionally or alternatively, the system 200 may detect a separation time between motion pulses 310 in an input command pattern 305, and the system 200 may determine that two or more motion pulses 310 are part of the input command pattern 305 based on the separation time between the motion pulses 310 being less than a threshold separation time. For example, the threshold separation time may be one second. As such, if a user produces two motion pulses 310 separated in time by 2 seconds, the system 200 may refrain from determining that the two motion pulses 310 are part of the same input command pattern 305 (e.g., the motion pulses were too far apart to be identified as a valid input command pattern 305).

In some embodiments, a user may perform multiple input command patterns 305 in succession (e.g., in a row) to input a first user input followed by one or more additional user inputs associated with the first user input. In some cases, an LED on the ring 104 may indicate that a first input command pattern 305 was detected and the system 200 is ready to detect additional input command patterns 305 associated with the first input command pattern 305. For example, the user may input a first input command pattern 305 associated with a command for tagging that the user is participating in or has participated in (e.g., engaged in) an outdoor activity. The system 200 may detect the first input command pattern 305 and light up an LED on the ring 104 to alert the user that the system 200 is ready to receive additional input command patterns 305 associated with tagging the outdoor activity. In some cases, the user may refrain from performing an additional input command pattern 305 within a time threshold (e.g., associated with receiving additional input command patterns 305) and the system 200 may tag the outdoor activity based off of the first input command pattern 305 (e.g., upon expiration of a timer associated with the time threshold). In some other cases, the user may perform an additional input command pattern 305, such as a second input command pattern 305, indicating the type of outdoor activity (e.g., hiking, running, biking, etc.). In some aspects, the system 200 may indicate to the user (e.g., provide feedback) whether user inputs have been successfully/unsuccessfully received. In some embodiments, different colors of LEDs and/or different patterns or combinations of flashing LEDs on the ring 104 may be used to indicate whether user inputs have been successfully/unsuccessfully received. Additionally, or alternatively, the system 200 may indicate whether user inputs have been successfully/unsuccessfully received via haptic feedback, audible feedback, or both. For example, one or more aspects of the system 200 may generate patterns or combinations of vibrations and/or tones to indicate whether user inputs have been successfully/unsuccessfully received.

In some embodiments, the system 200 may use multiple sensors to detect an input command pattern 305. For example, the system 200 may detect an input command pattern 305 based on an orientation of a user's hand wearing the ring 104. For example, a user may define a reference command pattern (e.g., in a command library described with reference to FIG. 4) that includes multiple taps performed while the ring is horizontal (e.g., while the user's palm of a hand wearing the wearable ring device is parallel to the ground). As such, the system 200 may use one or more motion sensors (such as motion sensors 245 and/or accelerometer sensors described with reference to FIG. 2) to detect the taps and to detect that the user's palm is horizontal.

In some aspects, the ring 104 may be configured to identify motion pulses 310 in different directions. Moreover, input command patterns 305 (and reference command patterns) may be defined to include motion pulses 310 in defined directions. For example, motion pulses 310 may be defined along one or more axes, such as x, y, and z-axes. In this example, a first motion pulse 310 may be defined based on motion data (e.g., acceleration data) in the positive y-axis, whereas a second motion pulse 310 may be defined based on motion data in the negative y-axis. For instance, a user may place their index finger and thumb on the top and bottom of the ring 104, and may first tap the ring 104 with their index finger, then with their thumb. In this example, the ring 104 may detect a first motion pulse 310 along the negative y-axis (due to the tap with the index finger), and a second motion pulse 310 along the positive y-axis (due to the tap with the thumb). In this example, the ring 104 may be configured to differentiate between the directions of the different taps.

Moreover, input command patterns 305 and reference command patterns may be defined as including taps in certain directions. For example, a user may define a reference command pattern as including three motion pulses 310 (e.g., three taps): (1) a first motion pulse in the negative y-direction, (2) a second tap in the negative y-direction, and (3) a third tap in the positive y-direction. In this example, in order to perform an input command pattern 305 associated with the reference command pattern, the user may tap the ring 104 twice with their index finger in the negative y-direction, then once with their thumb in the positive y-direction. Comparatively, if the user taps three times in the negative y-direction, the system 200 may determine that the input command pattern 305 including three motion pulses 310 in the negative y-direction does not match the reference command pattern (due to the last motion pulse 310 being in the negative y-direction, instead of in the positive y-direction).

As noted previously herein, user inputs may be associated with one or more actions, including inputting tags for taggable events, starting/ending workouts, starting/ending restorative or meditative movements, controlling/activating external devices, causing the ring 104 to perform measurements or activate certain sensors of the ring 104, or any combination thereof. For example, a reference command pattern may correspond to a user input for performing certain physiological measurements, such as measuring an instantaneous heart rate, performing a blood oxygen measurement, performing an ECG measurement, and the like. In this example, upon identifying that an input command pattern 305 matches the reference command pattern, the ring 104 may activate one or more sensors in order to perform the respective measurement (e.g., heart rate measurement, blood oxygen measurement, ECG measurement) associated with the reference command pattern.

Although motion pulses 310 are primarily described as being generated by a user "tapping" a wearable ring device such that resulting motion data exceeds the motion threshold 315, this is not to be regarded as a limitation of the present disclosure. In other words, motion pulses 310 may be generated and identified based on any motion data, including motion data generated by the user rotating the ring 104, performing a gesture (e.g., waving their hand up and down, side to side, clockwise, counterclockwise), and the like. Moreover, motion pulses 310 may be generated based on normal user movement throughout the day, including movement that is not intended as an input command. For example, the ring 104 may detect motion pulses 310 as a user knocks on a door, types on a computer keyboard, or adjusts their hair. However, such "unintentional" motion pulses 310 are unlikely to form an input command pattern 305 that will not match a reference command pattern, and the system 200 will therefore ignore or disregard unintentional input command patterns 305 that do not match a reference command pattern. Additionally or alternatively, the ring 104 may detect a quantity of "unintentional" motion pulses 310 which exceed a threshold and the system 200 may ignore or disregard unintentional input command patterns 305 based on the quantity exceeding a threshold (e.g., within a duration). For example, a user may type on a keyboard producing "unintentional" motion pulses 310 that may match a reference command pattern associated with a tapping hand gesture. However, the system 200 may detect that the quantity of motion pulses 310 (that are generated by typing on a keyboard) exceeds a threshold quantity (and/or threshold frequency), and may ignore the unintentional input command patterns 305. As such, by requiring input command patterns 305 to match reference command patterns in order for the system to identify a valid user input, techniques described herein may enable the system 200 to differentiate "normal" user movements from user movements that are intended to be user inputs.

Figure 4:
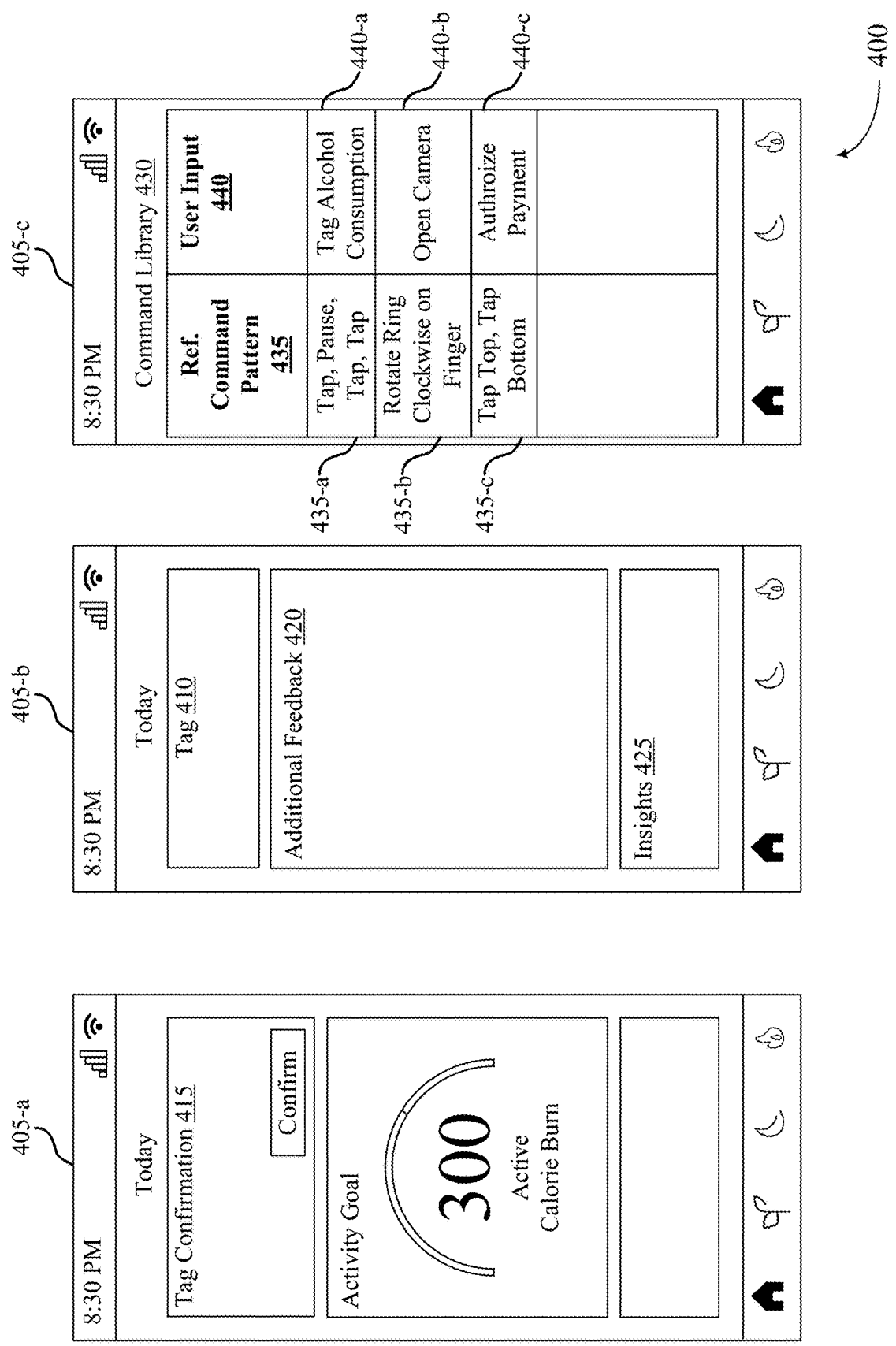
FIG. 4 illustrates an example of a graphical user interface (GUI) that supports ring-inputted commands in accordance with aspects of the present disclosure.

FIG. 4 illustrates an example of a GUI 400 that supports ring-inputted commands in accordance with aspects of the present disclosure. The GUI 400 may implement, or be implemented by, aspects of the system 100, the system 200, the command pattern 300, or any combination thereof. For example, the GUI 400 may include an example of the GUI included within a user device 106.

The GUI 400 illustrates a series of application pages 405 that may be displayed to the user via the GUI 400 (e.g., GUI illustrated in FIG. 2). Continuing with the example above, the system 200 may identify that an input command pattern 305 matches a reference command pattern associated with a user input. In this example, the user input may be for the system 200 to input a tag 410 (e.g., the reference command pattern causes the system 200 to input or generate the tag 410 for a taggable event). Upon identifying the user input (e.g., generating the tag 410), the user may be presented with the application page 405-*a*. As shown in FIG. 4, the application page 405-*a* may display an indication that the tag 410 was detected based on an associated input command pattern.

In some cases, the indication may include a tag confirmation 415 that may prompt the user to confirm or dismiss the tag 410 (e.g., confirm/deny whether the system 200 correctly detected the input command pattern associated with the tag 410 or confirm/deny that the tag 410 was the tag that the user intended to input). Additionally or alternatively, the tag confirmation 415 may display a confirmation message to the user indicating that the tag 410 was successfully recorded (e.g., automatically record the tag 410 without user confirmation).

In some implementations, the tag 410 may be recorded/logged in a database. For example, the tag 410 may be logged in an activity log for the user for the respective day. In some aspects, the system 200 may associate the tag 410 (e.g., taggable event) with physiological data collected from the user in order to identify trends or relationships between tagged events and the user's physiological data (e.g., determine that caffeine leads to poor quality sleep for the user). Moreover, in some cases, the tag 410 may be used to update (e.g., modify) one or more scores associated with the user (e.g., Sleep Score, Readiness Score). That is, data associated with the tag 410 may be used to update the scores for the user for the respective day that the tag 410 was detected. In some cases, the application page 405-*a* may display the one or more scores for the user for the respective day.

In some implementations, the system 200 may be configured to log, record, or otherwise recognize data associated with a tag 410 (e.g., user input for the taggable event) without explicit confirmation from a user. For example, in some cases, the system 200 may identify an input command pattern associated with a tag 410 with a sufficient degree of precision, accuracy, or reliability (e.g., probability of a detected motion pulse satisfying a motion threshold, such as a motion threshold 315). In such cases, the system 200 may log or otherwise record the tag 410 without displaying a prompt (e.g., the tag confirmation 415) to a user and/or receiving an explicit confirmation from the user. Additionally, the system 200 may perform an action (e.g., based on one or more instructions) associated with the tag 410 without displaying a prompt to a user and/or receiving an explicit confirmation from the user. For example, the system 200 may activate or deactivate one or more sensors of a wearable ring device, such as a ring 104, based on the tag 410.

In cases where the user dismisses the tag confirmation 415 (e.g., prompt) on the application page 405-*a*, the tag confirmation 415 may disappear, and the data from the (incorrectly) determined tag 410 may not be used to update the user's scores or logged in an activity log for the user for the respective day.

Conversely, in cases where the system 200 correctly identified the tag 410 (e.g., upon confirming the tag confirmation 415 on the application page 405-*a*), the user may access an application page 405-*b*. As shown in FIG. 4, the application page 405-*b* may display an indication of the tag 410 and prompt the user to input additional feedback 420 associated with the tag 410. For example, the user may perform an input command pattern associated with tagging alcohol consumption (e.g., the tag 410 is associated with alcohol consumption). As such, the application page 405-*b* may display "alcohol consumed" and may prompt the user to provide additional feedback 420, such as requesting the user to input the type of alcohol consumed or a duration of time over which the alcohol was consumed.

In some examples, the application page 405-*b* may display an indication of one or more tag based insights, such as insights 425, associated with the tag 410. For example, the application page 405-*b* may display an indication of physiological data associated with the tag 410 (e.g., collected prior to or following input of the tag 410). For example, upon detecting the tag 410, the ring 104 may collect additional physiological data associated with the tag 410 and display an indication of the additional physiological data to the user. By way of another example, the system may display insights 425 indicating whether the tag 410 positively or negatively impacted one or more of the users scores. For example, the application page 405-*b* may display, via the insights 425, an indication that the user tagged alcohol consumption within an hour of sleeping and the wearable ring device recorded an increase in sleep disruption during the associated sleep period, resulting in a decrease in the user's Sleep Score (e.g., the timing of the alcohol consumption negatively affected the user's Sleep Score).

Continuing with reference to FIG. 4, a user may be able to access a command library 430 on an application page 405-*c*. The command library 430 may display an indication of reference command patterns 435 and associated user inputs 440 (e.g., instructions based on user inputs). For example, user inputs 440 may correspond to tagging an event, causing a user device or external device (e.g., a television, an appliance, a thermostat, a speaker, a humidifier, a light source, a camera, or any combination thereof) to perform an action, tagging a current state of the user, among other command outputs. In some cases, one or more of the reference command patterns 435 and the associated user inputs 440 may be user defined. That is, the user may define (e.g., input) a reference command pattern 435 (e.g., by tapping the reference command pattern 435 on the ring 104) and define (e.g., select) an associated user input 440. Additionally or alternatively, one or more of the reference command patterns 435 and the associated user inputs 440 may be defined by the system 200. That is one or more of the reference command patterns 435 may include a default command pattern and may be associated with default user inputs 440 (e.g., ring 104 is pre-configured with a reference command pattern 435 for a user input 440 that starts a running workout). In some embodiments, the user may select reference command patterns 435 from a predefined list of reference command patterns 435, or may manually define/input customized reference command patterns 435 (e.g., via the user device 106 and/or by inputting the reference command patterns 435 via the ring 104). Additionally or alternatively, the user may select user inputs 440 from a predefined list of command patterns 435, or may manually define/input customized user inputs 440 (e.g., link a smart device that is to be controlled according to an identified user input 440).

The reference command patterns 435 may be based on the user interacting with the ring 104. Interacting with the ring 104 may include, but is not limited to, tapping on the wearable ring device, rotating the wearable ring device, performing a hand gesture using a hand wearing the ring 104, or any combination thereof. For example, a reference command pattern 435-*a* may be associated with a tap on the ring 104, followed by a pause (e.g., a one second pause), followed by two consecutive taps. A user may perform an input command pattern and the system may determine that the input command pattern matches the reference command pattern 435-*a* associated with a user input 440-*a* that causes the system 200 to tag alcohol consumption. As such, upon matching the input command pattern to the reference command pattern 435-*a*, the system 200 may tag that the user consumed alcohol.

In another example, a reference command pattern 435-*b* may be associated with rotating the ring 104 clockwise (e.g., past a rotation or degree threshold) on the finger of the user. Additionally, the reference command pattern 435-*b* may correspond to a user input 440-*b* that may cause the system 200 to open a camera application on a user device 106 associated with the ring 104 (or cause the user device to take a picture via the camera). In another example, a reference command pattern 435-*c* (e.g., a PIN reference command pattern) may be associated with tapping the top of the ring 104 followed by tapping the bottom of the ring 104. Additionally, the reference command pattern 435-*c* may correspond to a user input 440-*c* that may cause the system 200 to authorize a payment, or identify/authenticate the user.

Figure 5:
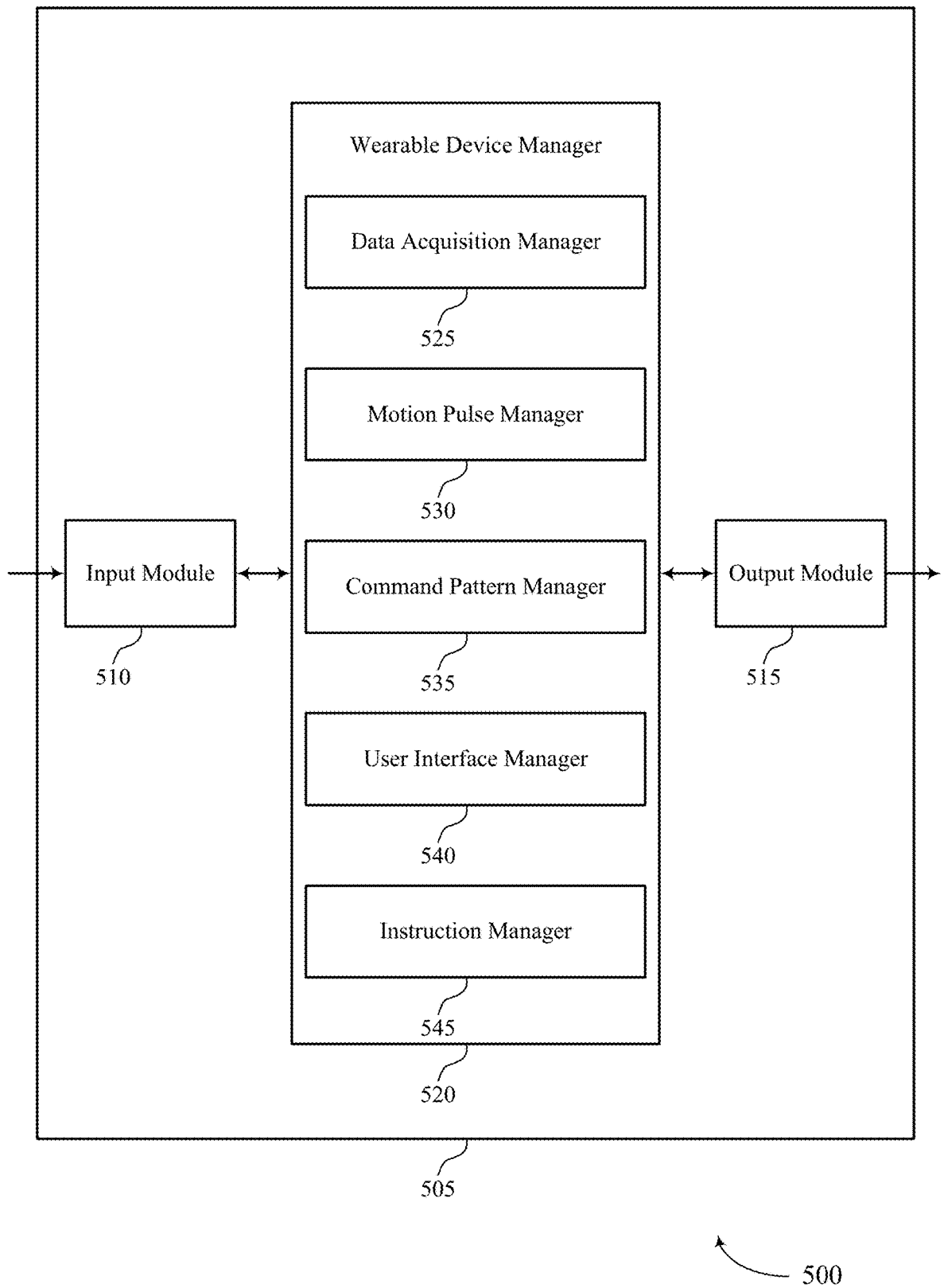
FIG. 5 shows a block diagram of an apparatus that supports ring-inputted commands in accordance with aspects of the present disclosure.

FIG. 5 shows a block diagram 500 of a device 505 that supports ring-inputted commands in accordance with aspects of the present disclosure. The device 505 may include an input module 510, an output module 515, and a wearable device manager 520. The device 505 may also include a processor. Each of these components may be in communication with one another (e.g., via one or more buses).

For example, the wearable device manager 520 may include a data acquisition manager 525, a motion pulse manager 530, a command pattern manager 535, a user interface manager 540, an instruction manager 545, or any combination thereof. In some examples, the wearable device manager 520, or various components thereof, may be configured to perform various operations (e.g., receiving, monitoring, transmitting) using or otherwise in cooperation with the input module 510, the output module 515, or both. For example, the wearable device manager 520 may receive information from the input module 510, send information to the output module 515, or be integrated in combination with the input module 510, the output module 515, or both to receive information, transmit information, or perform various other operations as described herein.

The wearable device manager 520 may support device-inputted commands in accordance with examples as disclosed herein. The data acquisition manager 525 may be configured as or otherwise support a means for acquiring physiological data associated with a user via a wearable ring device, the physiological data comprising at least motion data collected via one or more acceleration sensors of the wearable ring device. The motion pulse manager 530 may be configured as or otherwise support a means for identifying a plurality of motion pulses based at least in part on the physiological data, wherein each motion pulse of the plurality of motion pulses comprises motion data that is greater than a motion threshold. The command pattern manager 535 may be configured as or otherwise support a means for identifying an input command pattern comprising at least one motion pulse of the plurality of motion pulses based at least in part on the at least one motion pulse being preceded by a first static period and followed by a second static period in a time domain. The user interface manager 540 may be configured as or otherwise support a means for identifying one or more user inputs based at least in part on the input command pattern matching a reference command pattern. The instruction manager 545 may be configured as or otherwise support a means for generating one or more instructions based at least in part on identifying the one or more user inputs.

Figure 6:
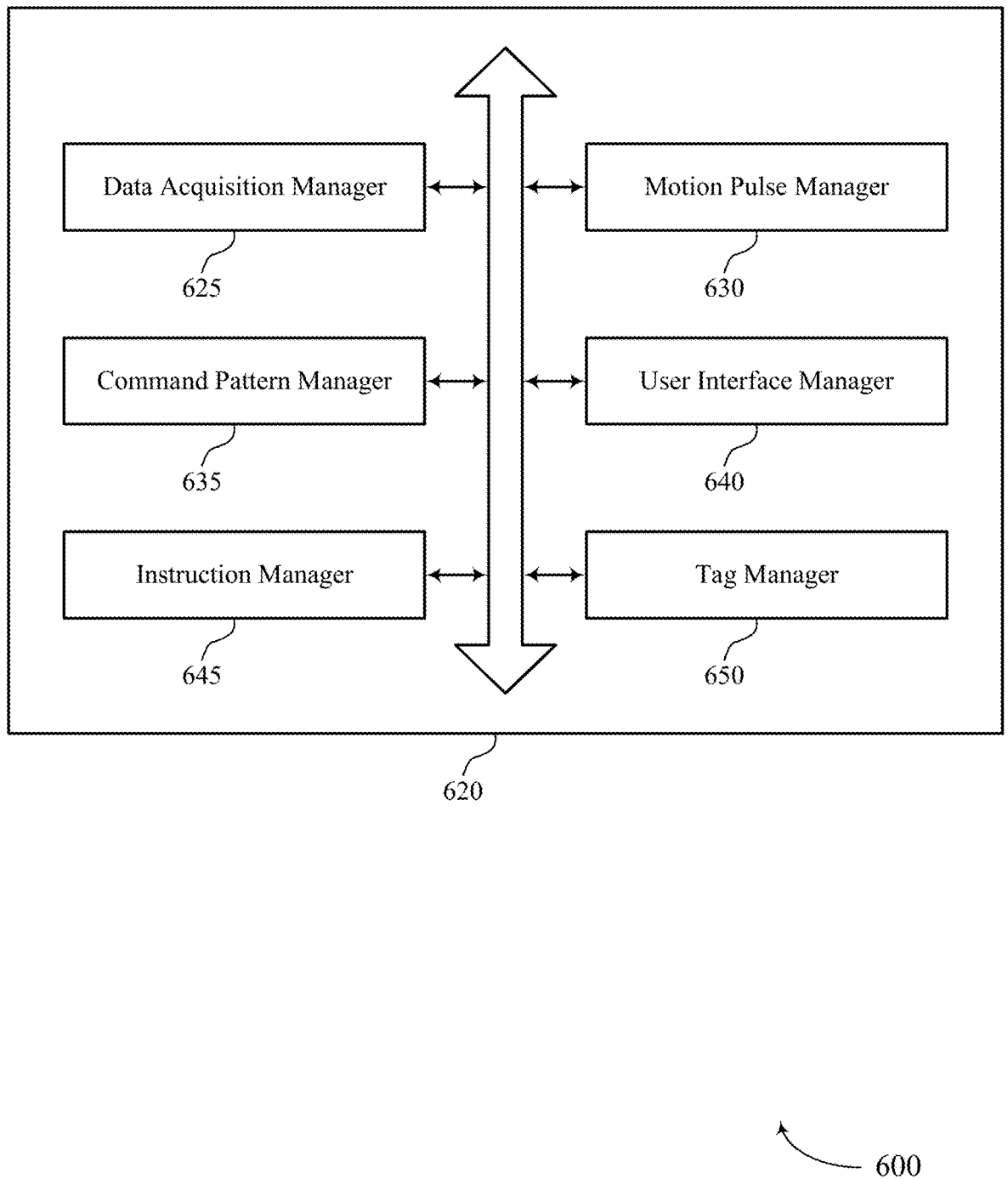
FIG. 6 shows a block diagram of a wearable device manager that supports ring-inputted commands in accordance with aspects of the present disclosure.

FIG. 6 shows a block diagram 600 of a wearable device manager 620 that supports ring-inputted commands in accordance with aspects of the present disclosure. The wearable device manager 620 may be an example of aspects of a wearable device manager or a wearable device manager 520, or both, as described herein. The wearable device manager 620, or various components thereof, may be an example of means for performing various aspects of ring-inputted commands as described herein. For example, the wearable device manager 620 may include a data acquisition manager 625, a motion pulse manager 630, a command pattern manager 635, a user interface manager 640, an instruction manager 645, a tag manager 650, or any combination thereof. Each of these components may communicate, directly or indirectly, with one another (e.g., via one or more buses).

The wearable device manager 620 may support device-inputted commands in accordance with examples as disclosed herein. The data acquisition manager 625 may be configured as or otherwise support a means for acquiring physiological data associated with a user via a wearable ring device, the physiological data comprising at least motion data collected via one or more acceleration sensors of the wearable ring device. The motion pulse manager 630 may be configured as or otherwise support a means for identifying a plurality of motion pulses based at least in part on the physiological data, wherein each motion pulse of the plurality of motion pulses comprises motion data that is greater than a motion threshold. The command pattern manager 635 may be configured as or otherwise support a means for identifying an input command pattern comprising at least one motion pulse of the plurality of motion pulses based at least in part on the at least one motion pulse being preceded by a first static period and followed by a second static period in a time domain. The user interface manager 640 may be configured as or otherwise support a means for identifying one or more user inputs based at least in part on the input command pattern matching a reference command pattern. The instruction manager 645 may be configured as or otherwise support a means for generating one or more instructions based at least in part on identifying the one or more user inputs.

In some examples, the motion pulse manager 630 may be configured as or otherwise support a means for identifying the first static period based at least in part on first motion data being less than or equal to a second motion threshold for a first time interval prior to the at least one motion pulse in the time domain. In some examples, the motion pulse manager 630 may be configured as or otherwise support a means for identifying the second static period based at least in part on second motion data being less than or equal to the second motion threshold for a second time interval subsequent to the at least one motion pulse in the time domain.

In some examples, the user interface manager 640 may be configured as or otherwise support a means for receiving an additional user input comprising an indication of the reference command pattern. In some examples, the command pattern manager 635 may be configured as or otherwise support a means for storing the reference command pattern based at least in part on the additional user input, wherein identifying the one or more user inputs is based at least in part on comparing the input command pattern to the stored reference command pattern.

In some examples, to support identifying the input command pattern, the motion pulse manager 630 may be configured as or otherwise support a means for identifying a first motion pulse of the plurality of motion pulses, wherein the first motion pulse is preceded by the first static period and followed by the second static period. In some examples, to support identifying the input command pattern, the motion pulse manager 630 may be configured as or otherwise support a means for identifying one or more additional motion pulses of the plurality of motion pulses, wherein each motion pulse of the one or more additional motion pulses is preceded and followed by one or more respective sets of static periods.

In some examples, the motion pulse manager 630 may be configured as or otherwise support a means for identifying a time interval between the first motion pulse and the one or more additional motion pulses, wherein identifying the input command pattern, identifying the one or more user inputs, or both, is based at least in part on the time interval satisfying a threshold time interval.

In some examples, the input command pattern is based at least in part on the first motion pulse and the one or more additional motion pulses.

In some examples, the command pattern manager 635 may be configured as or otherwise support a means for identifying the input command pattern based at least in part on respective durations of the first static period, the second static period, and the one or more respective sets of static periods each satisfying one or more duration thresholds.

In some examples, the one or more additional motion pulses comprises at least two motion pulses.

In some examples, the command pattern manager 635 may be configured as or otherwise support a means for identifying a first duration associated with the input command pattern. In some examples, the command pattern manager 635 may be configured as or otherwise support a means for comparing the first duration associated with the input command pattern with a second duration associated with the reference command pattern, wherein identifying the one or more user inputs is based at least in part on the comparison.

In some examples, the reference command pattern is associated with the one or more instructions. In some examples, generating the one or more instructions is based at least in part on the input command pattern matching the reference command pattern.

In some examples, the reference command pattern is included within a plurality of reference command patterns. In some examples, each reference command pattern of the plurality of reference command patterns is associated with a corresponding set of instructions.

In some examples, the reference command pattern comprises a default reference command pattern associated with the wearable ring device.

In some examples, the command pattern manager 635 may be configured as or otherwise support a means for comparing the input command pattern to a plurality of reference command patterns including the reference command pattern. In some examples, the command pattern manager 635 may be configured as or otherwise support a means for matching the input command pattern to the reference command pattern based at least in part on the comparison, wherein identifying the one or more user inputs is based at least in part on the matching.

In some examples, the tag manager 650 may be configured as or otherwise support a means for identifying, based at least in part on the one or more user inputs, a taggable event indicating an activity the user is or has engaged in, wherein generating the one or more instructions is based at least in part on the taggable event. In some examples, the tag manager 650 may be configured as or otherwise support a means for associating the taggable event with at least a portion of the acquired physiological data based at least in part on the one or more instructions.

In some examples, the user interface manager 640 may be configured as or otherwise support a means for causing a graphical user interface of a user device associated with the wearable ring device to prompt the user to provide feedback associated with the identified taggable event.

In some examples, the instruction manager 645 may be configured as or otherwise support a means for causing the wearable ring device, a user device associated with the wearable ring device, an external device, or any combination thereof, to perform one or more actions based at least in part on the one or more instructions.

In some examples, the one or more actions comprises selectively activating or deactivating one or more sensors of the wearable ring device.

In some examples, the external device comprises a television, an appliance, a thermostat, a speaker, a humidifier, a light source, a camera, or any combination thereof.

In some examples, the data acquisition manager 625 may be configured as or otherwise support a means for acquiring additional physiological data associated with the user via the wearable ring device based at least in part on the one or more instructions.

In some examples, the plurality of motion pulses are based at least in part on the user performing an action. In some examples, the action comprises tapping on the wearable ring device, rotating the wearable ring device, a hand gesture, or any combination thereof.

In some examples, at least one motion pulse associated with the input command pattern comprises a plurality of motion pulses associated with one or more hand gestures of the user.

In some examples, the wearable ring device collects the physiological data from the user using based on arterial blood flow.

Figure 7:
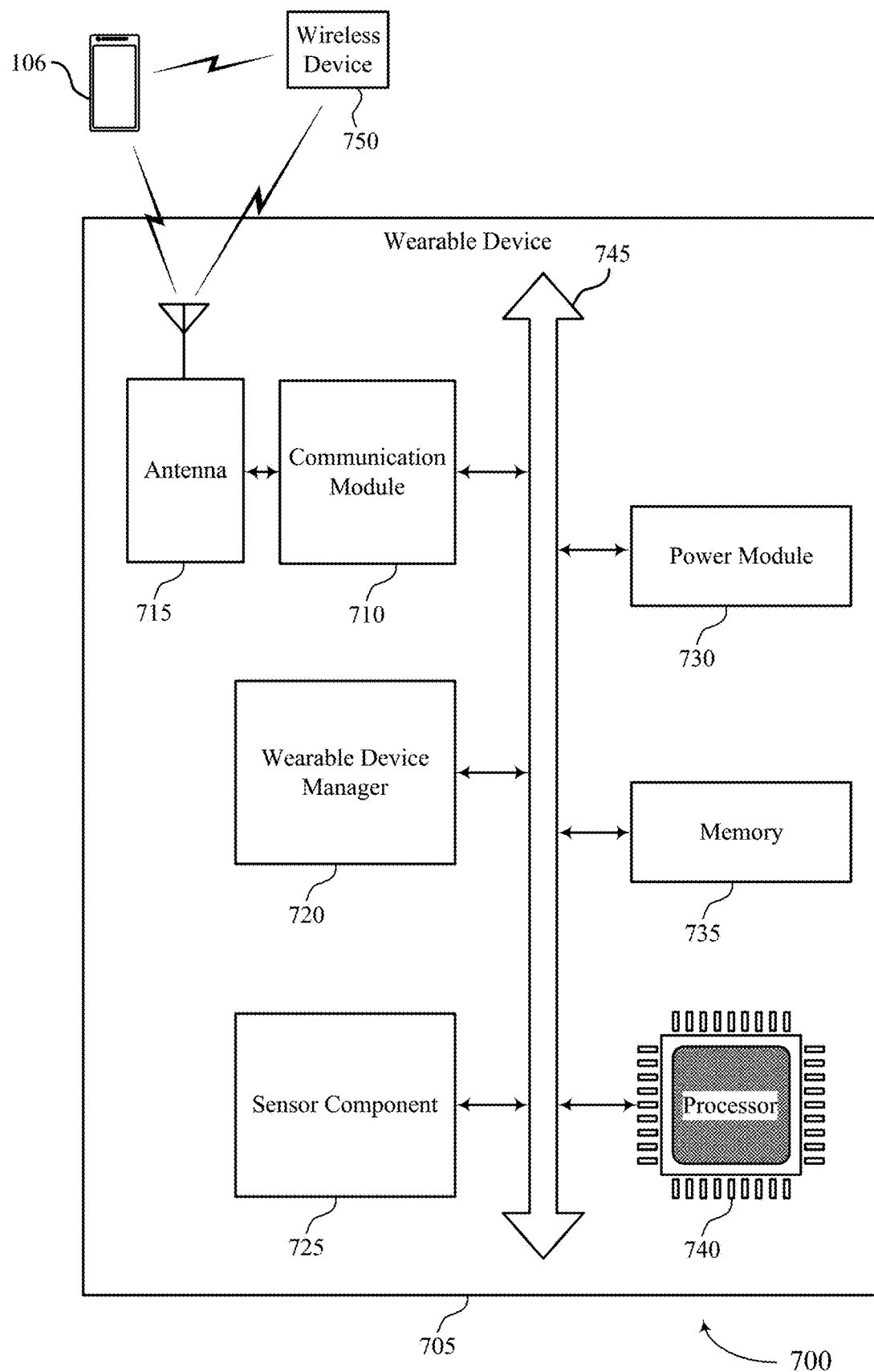
FIG. 7 shows a diagram of a system including a device that supports ring-inputted commands in accordance with aspects of the present disclosure.

FIG. 7 shows a diagram of a system 700 including a device 705 that supports ring-inputted commands in accordance with aspects of the present disclosure. The device 705 may be an example of or include the components of a device 505 as described herein. The device 705 may include an example of a wearable device 104, as described previously herein. The device 705 may include components for bi-directional communications including components for transmitting and receiving communications with a user device 106 and a server 110, such as a wearable device manager 720, a communication module 710, an antenna 715, a sensor component 725, a power module 730, a memory 735, a processor 740, and a wireless device 750. These components may be in electronic communication or otherwise coupled (e.g., operatively, communicatively, functionally, electronically, electrically) via one or more buses (e.g., a bus 745).

The wearable device manager 720 may support device-inputted commands in accordance with examples as disclosed herein. For example, the wearable device manager 720 may be configured as or otherwise support a means for acquiring physiological data associated with a user via a wearable ring device, the physiological data comprising at least motion data collected via one or more acceleration sensors of the wearable ring device. The wearable device manager 720 may be configured as or otherwise support a means for identifying a plurality of motion pulses based at least in part on the physiological data, wherein each motion pulse of the plurality of motion pulses comprises motion data that is greater than a motion threshold. The wearable device manager 720 may be configured as or otherwise support a means for identifying an input command pattern comprising at least one motion pulse of the plurality of motion pulses based at least in part on the at least one motion pulse being preceded by a first static period and followed by a second static period in a time domain. The wearable device manager 720 may be configured as or otherwise support a means for identifying one or more user inputs based at least in part on the input command pattern matching a reference command pattern. The wearable device manager 720 may be configured as or otherwise support a means for generating one or more instructions based at least in part on identifying the one or more user inputs.

By including or configuring the wearable device manager 720 in accordance with examples as described herein, the device 705 may support techniques for ring-inputted commands. In particular, techniques described herein may support identifying command patterns inputted by a user via a wearable ring device. By providing the user with the ability to provide user input through command patterns, techniques described herein may enable the user to efficiently input additional data or feedback associated with the user (e.g., tags), which may result in increased input of additional data or feedback and improved health insights. Additionally, techniques described herein may enable the user to efficiently perform a variety of operations.

Figure 8:
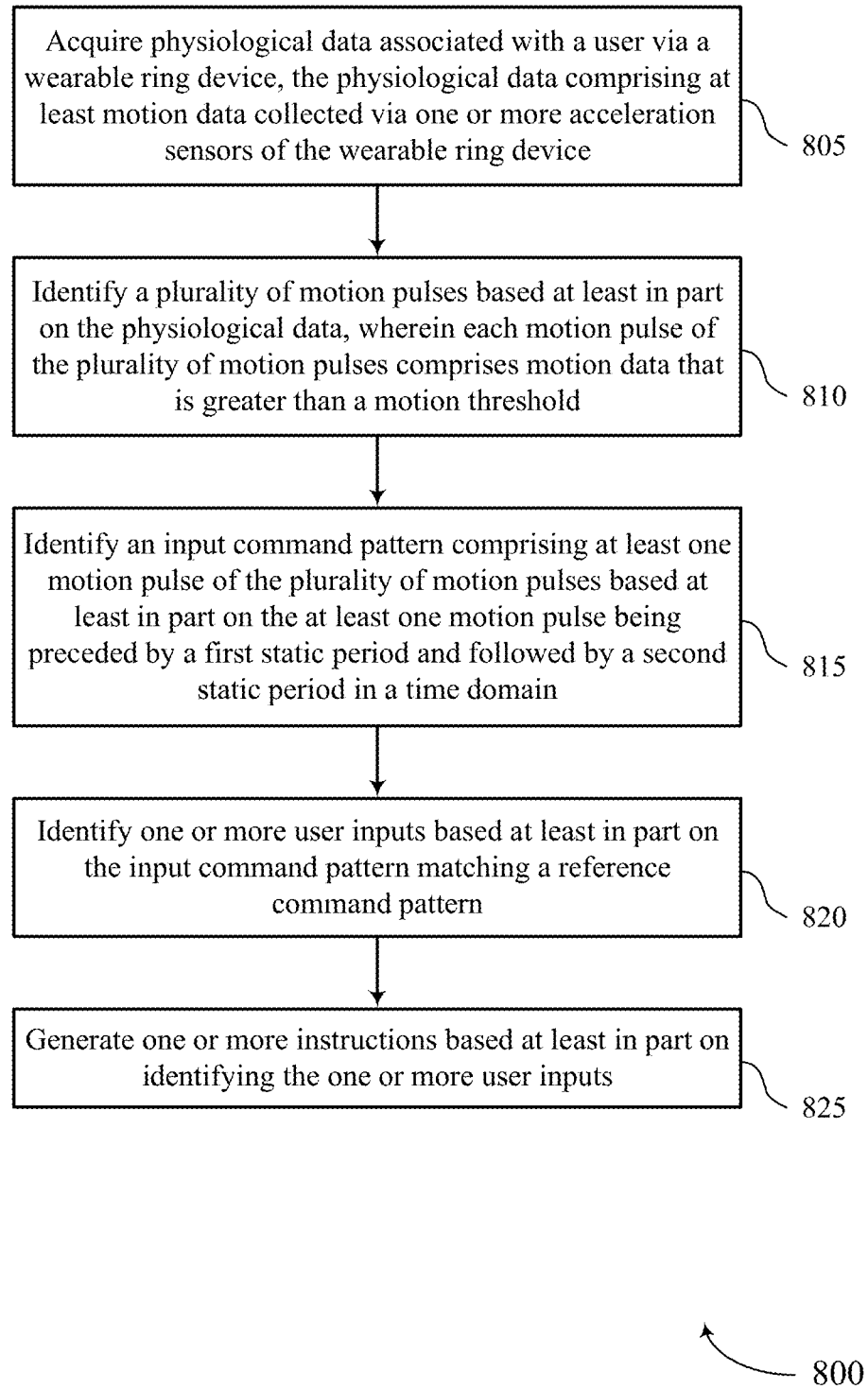
FIGS. 8 and 9 show flowcharts illustrating methods that support ring-inputted commands in accordance with aspects of the present disclosure.

FIG. 8 shows a flowchart illustrating a method 800 that supports ring-inputted commands in accordance with aspects of the present disclosure. The operations of the method 800 may be implemented by a wearable device or its components as described herein. For example, the operations of the method 800 may be performed by a wearable device as described with reference to FIGS. 1 through 7. In some examples, a wearable device may execute a set of instructions to control the functional elements of the wearable device to perform the described functions. Additionally, or alternatively, the wearable device may perform aspects of the described functions using special-purpose hardware.

At 805, the method may include acquiring physiological data associated with a user via a wearable ring device, the physiological data comprising at least motion data collected via one or more acceleration sensors of the wearable ring device. The operations of 805 may be performed in accordance with examples as disclosed herein. In some examples, aspects of the operations of 805 may be performed by a data acquisition manager 625 as described with reference to FIG. 6.

At 810, the method may include identifying a plurality of motion pulses based at least in part on the physiological data, wherein each motion pulse of the plurality of motion pulses comprises motion data that is greater than a motion threshold. The operations of 810 may be performed in accordance with examples as disclosed herein. In some examples, aspects of the operations of 810 may be performed by a motion pulse manager 630 as described with reference to FIG. 6.

At 815, the method may include identifying an input command pattern comprising at least one motion pulse of the plurality of motion pulses based at least in part on the at least one motion pulse being preceded by a first static period and followed by a second static period in a time domain. The operations of 815 may be performed in accordance with examples as disclosed herein. In some examples, aspects of the operations of 815 may be performed by a command pattern manager 635 as described with reference to FIG. 6.

At 820, the method may include identifying one or more user inputs based at least in part on the input command pattern matching a reference command pattern. The operations of 820 may be performed in accordance with examples as disclosed herein. In some examples, aspects of the operations of 820 may be performed by a user interface manager 640 as described with reference to FIG. 6.

At 825, the method may include generating one or more instructions based at least in part on identifying the one or more user inputs. The operations of 825 may be performed in accordance with examples as disclosed herein. In some examples, aspects of the operations of 825 may be performed by an instruction manager 645 as described with reference to FIG. 6.

Figure 9:
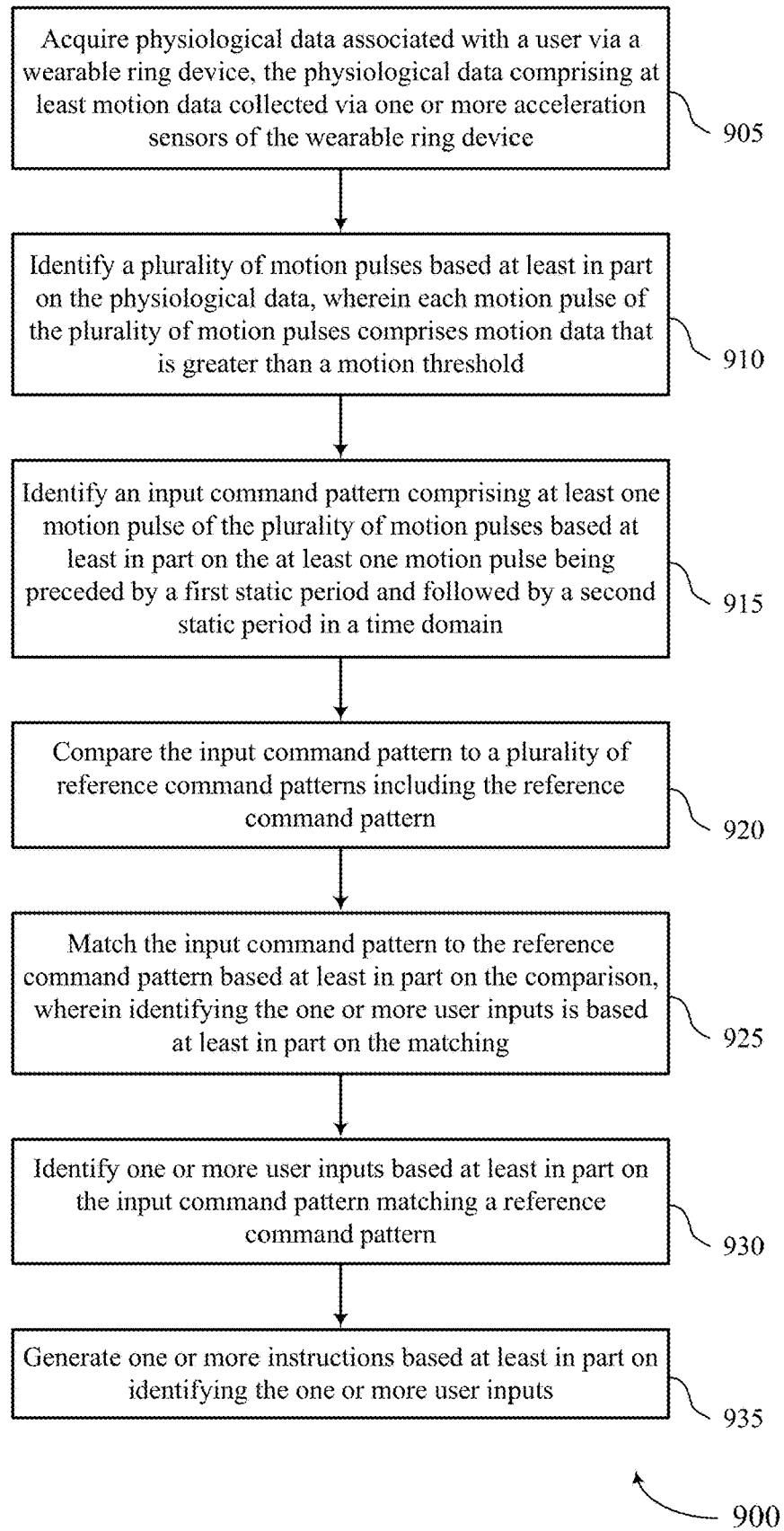

FIG. 9 shows a flowchart illustrating a method 900 that supports ring-inputted commands in accordance with aspects of the present disclosure. The operations of the method 900 may be implemented by a wearable device or its components as described herein. For example, the operations of the method 900 may be performed by a wearable device as described with reference to FIGS. 1 through 7. In some examples, a wearable device may execute a set of instructions to control the functional elements of the wearable device to perform the described functions. Additionally, or alternatively, the wearable device may perform aspects of the described functions using special-purpose hardware.

At 905, the method may include acquiring physiological data associated with a user via a wearable ring device, the physiological data comprising at least motion data collected via one or more acceleration sensors of the wearable ring device. The operations of 905 may be performed in accordance with examples as disclosed herein. In some examples, aspects of the operations of 905 may be performed by a data acquisition manager 625 as described with reference to FIG. 6.

At 910, the method may include identifying a plurality of motion pulses based at least in part on the physiological data, wherein each motion pulse of the plurality of motion pulses comprises motion data that is greater than a motion threshold. The operations of 910 may be performed in accordance with examples as disclosed herein. In some examples, aspects of the operations of 910 may be performed by a motion pulse manager 630 as described with reference to FIG. 6.

At 915, the method may include identifying an input command pattern comprising at least one motion pulse of the plurality of motion pulses based at least in part on the at least one motion pulse being preceded by a first static period and followed by a second static period in a time domain. The operations of 915 may be performed in accordance with examples as disclosed herein. In some examples, aspects of the operations of 915 may be performed by a command pattern manager 635 as described with reference to FIG. 6.

At 920, the method may include comparing the input command pattern to a plurality of reference command patterns including the reference command pattern. The operations of 920 may be performed in accordance with examples as disclosed herein. In some examples, aspects of the operations of 920 may be performed by a command pattern manager 635 as described with reference to FIG. 6.

At 925, the method may include matching the input command pattern to the reference command pattern based at least in part on the comparison, wherein identifying the one or more user inputs is based at least in part on the matching. The operations of 925 may be performed in accordance with examples as disclosed herein. In some examples, aspects of the operations of 925 may be performed by a command pattern manager 635 as described with reference to FIG. 6.

At 930, the method may include identifying one or more user inputs based at least in part on the input command pattern matching a reference command pattern. The operations of 930 may be performed in accordance with examples as disclosed herein. In some examples, aspects of the operations of 930 may be performed by a user interface manager 640 as described with reference to FIG. 6.

At 935, the method may include generating one or more instructions based at least in part on identifying the one or more user inputs. The operations of 935 may be performed in accordance with examples as disclosed herein. In some examples, aspects of the operations of 935 may be performed by an instruction manager 645 as described with reference to FIG. 6.

It should be noted that the methods described above describe possible implementations, and that the operations and the steps may be rearranged or otherwise modified and that other implementations are possible. Furthermore, aspects from two or more of the methods may be combined.

A method for device-inputted commands is described. The method may include acquiring physiological data associated with a user via a wearable ring device, the physiological data comprising at least motion data collected via one or more acceleration sensors of the wearable ring device, identifying a plurality of motion pulses based at least in part on the physiological data, wherein each motion pulse of the plurality of motion pulses comprises motion data that is greater than a motion threshold, identifying an input command pattern comprising at least one motion pulse of the plurality of motion pulses based at least in part on the at least one motion pulse being preceded by a first static period and followed by a second static period in a time domain, identifying one or more user inputs based at least in part on the input command pattern matching a reference command pattern, and generating one or more instructions based at least in part on identifying the one or more user inputs.

An apparatus for device-inputted commands is described. The apparatus may include a processor, memory coupled with the processor, and instructions stored in the memory. The instructions may be executable by the processor to cause the apparatus to acquire physiological data associated with a user via a wearable ring device, the physiological data comprising at least motion data collected via one or more acceleration sensors of the wearable ring device, identify a plurality of motion pulses based at least in part on the physiological data, wherein each motion pulse of the plurality of motion pulses comprises motion data that is greater than a motion threshold, identify an input command pattern comprising at least one motion pulse of the plurality of motion pulses based at least in part on the at least one motion pulse being preceded by a first static period and followed by a second static period in a time domain, identify one or more user inputs based at least in part on the input command pattern matching a reference command pattern, and generate one or more instructions based at least in part on identifying the one or more user inputs.

Another apparatus for device-inputted commands is described. The apparatus may include means for acquiring physiological data associated with a user via a wearable ring device, the physiological data comprising at least motion data collected via one or more acceleration sensors of the wearable ring device, means for identifying a plurality of motion pulses based at least in part on the physiological data, wherein each motion pulse of the plurality of motion pulses comprises motion data that is greater than a motion threshold, means for identifying an input command pattern comprising at least one motion pulse of the plurality of motion pulses based at least in part on the at least one motion pulse being preceded by a first static period and followed by a second static period in a time domain, means for identifying one or more user inputs based at least in part on the input command pattern matching a reference command pattern, and means for generating one or more instructions based at least in part on identifying the one or more user inputs.

A non-transitory computer-readable medium storing code for device-inputted commands is described. The code may include instructions executable by a processor to acquire physiological data associated with a user via a wearable ring device, the physiological data comprising at least motion data collected via one or more acceleration sensors of the wearable ring device, identify a plurality of motion pulses based at least in part on the physiological data, wherein each motion pulse of the plurality of motion pulses comprises motion data that is greater than a motion threshold, identify an input command pattern comprising at least one motion pulse of the plurality of motion pulses based at least in part on the at least one motion pulse being preceded by a first static period and followed by a second static period in a time domain, identify one or more user inputs based at least in part on the input command pattern matching a reference command pattern, and generate one or more instructions based at least in part on identifying the one or more user inputs.

Some examples of the method, apparatuses, and non-transitory computer-readable medium described herein may further include operations, features, means, or instructions for identifying the first static period based at least in part on first motion data being less than or equal to a second motion threshold for a first time interval prior to the at least one motion pulse in the time domain and identifying the second static period based at least in part on second motion data being less than or equal to the second motion threshold for a second time interval subsequent to the at least one motion pulse in the time domain.

Some examples of the method, apparatuses, and non-transitory computer-readable medium described herein may further include operations, features, means, or instructions for receiving an additional user input comprising an indication of the reference command pattern and storing the reference command pattern based at least in part on the additional user input, wherein identifying the one or more user inputs may be based at least in part on comparing the input command pattern to the stored reference command pattern.

In some examples of the method, apparatuses, and non-transitory computer-readable medium described herein, identifying the input command pattern may include operations, features, means, or instructions for identifying a first motion pulse of the plurality of motion pulses, wherein the first motion pulse may be preceded by the first static period and followed by the second static period and identifying one or more additional motion pulses of the plurality of motion pulses, wherein each motion pulse of the one or more additional motion pulses may be preceded and followed by one or more respective sets of static periods.

Some examples of the method, apparatuses, and non-transitory computer-readable medium described herein may further include operations, features, means, or instructions for identifying a time interval between the first motion pulse and the one or more additional motion pulses, wherein identifying the input command pattern, identifying the one or more user inputs, or both, may be based at least in part on the time interval satisfying a threshold time interval.

In some examples of the method, apparatuses, and non-transitory computer-readable medium described herein, the input command pattern may be based at least in part on the first motion pulse and the one or more additional motion pulses.

Some examples of the method, apparatuses, and non-transitory computer-readable medium described herein may further include operations, features, means, or instructions for identifying the input command pattern based at least in part on respective durations of the first static period, the second static period, and the one or more respective sets of static periods each satisfying one or more duration thresholds.

In some examples of the method, apparatuses, and non-transitory computer-readable medium described herein, the one or more additional motion pulses comprises at least two motion pulses.

Some examples of the method, apparatuses, and non-transitory computer-readable medium described herein may further include operations, features, means, or instructions for identifying a first duration associated with the input command pattern and comparing the first duration associated with the input command pattern with a second duration associated with the reference command pattern, wherein identifying the one or more user inputs may be based at least in part on the comparison.

In some examples of the method, apparatuses, and non-transitory computer-readable medium described herein, the reference command pattern may be associated with the one or more instructions and generating the one or more instructions may be based at least in part on the input command pattern matching the reference command pattern.

In some examples of the method, apparatuses, and non-transitory computer-readable medium described herein, the reference command pattern may be included within a plurality of reference command patterns and each reference command pattern of the plurality of reference command patterns may be associated with a corresponding set of instructions.

In some examples of the method, apparatuses, and non-transitory computer-readable medium described herein, the reference command pattern comprises a default reference command pattern associated with the wearable ring device.

Some examples of the method, apparatuses, and non-transitory computer-readable medium described herein may further include operations, features, means, or instructions for comparing the input command pattern to a plurality of reference command patterns including the reference command pattern and matching the input command pattern to the reference command pattern based at least in part on the comparison, wherein identifying the one or more user inputs may be based at least in part on the matching.

Some examples of the method, apparatuses, and non-transitory computer-readable medium described herein may further include operations, features, means, or instructions for identifying, based at least in part on the one or more user inputs, a taggable event indicating an activity the user may be or may have engaged in, wherein generating the one or more instructions may be based at least in part on the taggable event and associating the taggable event with at least a portion of the acquired physiological data based at least in part on the one or more instructions.

Some examples of the method, apparatuses, and non-transitory computer-readable medium described herein may further include operations, features, means, or instructions for causing a graphical user interface of a user device associated with the wearable ring device to prompt the user to provide feedback associated with the identified taggable event.

Some examples of the method, apparatuses, and non-transitory computer-readable medium described herein may further include operations, features, means, or instructions for causing the wearable ring device, a user device associated with the wearable ring device, an external device, or any combination thereof, to perform one or more actions based at least in part on the one or more instructions.

In some examples of the method, apparatuses, and non-transitory computer-readable medium described herein, the one or more actions comprises selectively activating or deactivating one or more sensors of the wearable ring device.

In some examples of the method, apparatuses, and non-transitory computer-readable medium described herein, the external device comprises a television, an appliance, a thermostat, a speaker, a humidifier, a light source, a camera, or any combination thereof.

Some examples of the method, apparatuses, and non-transitory computer-readable medium described herein may further include operations, features, means, or instructions for acquiring additional physiological data associated with the user via the wearable ring device based at least in part on the one or more instructions.

In some examples of the method, apparatuses, and non-transitory computer-readable medium described herein, the plurality of motion pulses may be based at least in part on the user performing an action and the action comprises tapping on the wearable ring device, rotating the wearable ring device, a hand gesture, or any combination thereof.

In some examples of the method, apparatuses, and non-transitory computer-readable medium described herein, at least one motion pulse associated with the input command pattern comprises a plurality of motion pulses associated with one or more hand gestures of the user.

In some examples of the method, apparatuses, and non-transitory computer-readable medium described herein, the wearable ring device collects the physiological data from the user using based on arterial blood flow.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers.

Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method for device-inputted commands, comprising:
acquiring physiological data associated with a user via a wearable ring device, the physiological data comprising at least motion data collected via one or more acceleration sensors of the wearable ring device;
identifying a plurality of motion pulses based at least in part on the motion data, wherein each motion pulse of the plurality of motion pulses comprises motion data that is greater than a motion threshold;
identifying a set of motion pulses from the plurality of motion pulses, wherein identifying the set of motion pulses comprises:
identifying a first subset of motion pulses from the plurality of motion pulses that are each preceded by a first static period and followed by a second static period in a time domain, and a second subset of motion pulses from the plurality of motion pulses that are not preceded or followed by a respective static period in the time domain, wherein the set of motion pulses includes the first subset of motion pulses and excludes the second subset of motion pulses; and
identifying a third subset of motion pulses from the plurality of motion pulses that exhibit a separation time between sequential motion pulses that fails to satisfy one or more threshold separation times, wherein the set of motion pulses excludes the third subset of motion pulses;
identifying one or more input command patterns associated with the set of motion pulses for comparison to a plurality of reference command patterns based at least in part on including the first subset of motion pulses within the set of motion pulses, and excluding the second and third subsets of motion pulses from the set of motion pulses;
comparing the one or more input command patterns to the plurality of reference command patterns;
identifying a device-inputted command based at least in part on an input command pattern of the one or more input command patterns matching a reference command pattern from the plurality of reference command patterns; and
generating one or more instructions based at least in part on identifying the device-inputted command.

2. The method of claim 1, further comprising:
identifying the first static period of a respective motion pulse of the first subset of motion pulses based at least in part on first motion data being less than or equal to a second motion threshold for a first time interval prior to the respective motion pulse in the time domain; and
identifying the second static period of the respective motion pulse of the first subset of motion pulses based at least in part on second motion data being less than or equal to the second motion threshold for a second time interval subsequent to the respective motion pulse in the time domain.

3. The method of claim 1, further comprising:
receiving a user input comprising an indication of the reference command pattern; and
storing the reference command pattern based at least in part on the user input, wherein identifying the device-inputted command is based at least in part on comparing the input command pattern to the stored reference command pattern.

4. The method of claim 1, wherein identifying the first subset of motion pulses as being associated with one or more input command patterns further comprises:
identifying a first motion pulse of the plurality of motion pulses, wherein the first motion pulse is preceded by the first static period and followed by the second static period; and
identifying one or more additional motion pulses of the plurality of motion pulses, wherein each motion pulse of the one or more additional motion pulses is preceded and followed by one or more respective sets of static periods.

5. The method of claim 4, further comprising:
identifying a time interval between the first motion pulse and the one or more additional motion pulses, wherein identifying the input command pattern, identifying the device-inputted command, or both, is based at least in part on the time interval satisfying a threshold time interval.

6. The method of claim 4, wherein the input command pattern of the one or more input command patterns comprises the first motion pulse and the one or more additional motion pulses.

7. The method of claim 4, further comprising:
identifying the input command pattern of the one or more input command patterns for comparison to the plurality of reference command patterns based at least in part on respective durations of the first static period, the second static period, and the one or more respective sets of static periods each being greater than a first duration threshold and less than a second duration threshold.

8. The method of claim 4, wherein the one or more additional motion pulses comprises at least two motion pulses.

9. The method of claim 1, further comprising:
identifying a first duration associated with the input command pattern; and
comparing the first duration associated with the input command pattern with a second duration associated with the reference command pattern, wherein identifying the device-inputted command is based at least in part on comparing the first duration with the second duration.

10. The method of claim 1, wherein the reference command pattern is associated with the one or more instructions, and wherein generating the one or more instructions is based at least in part on the input command pattern matching the reference command pattern.

11. The method of claim 1, wherein each reference command pattern of the plurality of reference command patterns is associated with a corresponding set of instructions.

12. The method of claim 1, wherein the reference command pattern comprises a default reference command pattern associated with the wearable ring device.

13. The method of claim 1, further comprising:

matching the input command pattern of the one or more input command patterns to the reference command pattern based at least in part on comparing the one or more input command patterns to a plurality of reference command patterns, wherein identifying the device-inputted command is based at least in part on the matching.

14. The method of claim 1, further comprising:

identifying, based at least in part on identifying the device-inputted command, a taggable event indicating an activity the user is or has engaged in, wherein generating the one or more instructions is based at least in part on the taggable event; and associating the taggable event with at least a portion of the acquired physiological data based at least in part on the one or more instructions.

15. The method of claim 1, wherein the first static period and the second static period comprise periods that the wearable ring device is relatively motionless.

16. The method of claim 1, further comprising:
causing the wearable ring device, a user device associated with the wearable ring device, an external device, or any combination thereof, to perform one or more actions based at least in part on the one or more instructions.

17. The method of claim 16, wherein the one or more actions comprises selectively activating or deactivating one or more sensors of the wearable ring device.

18. The method of claim 16, wherein the external device comprises a television, an appliance, a thermostat, a speaker, a humidifier, a light source, a camera, or any combination thereof.

19. The method of claim 1, wherein the one or more input command patterns are based at least in part on the user performing an action, wherein the action comprises tapping on the wearable ring device, rotating the wearable ring device, a hand gesture, or any combination thereof.

20. The method of claim 1, wherein the second and third subset of motion pulses are excluded based at least in part on the second and third subset of motion pulses not being associated with the one or more input command patterns.

* * * * *